US008924236B2

(12) United States Patent
Marchosky

(10) Patent No.: US 8,924,236 B2
(45) Date of Patent: Dec. 30, 2014

(54) RECORD SYSTEM

(75) Inventor: J. Alexander Marchosky, Chesterfield, MO (US)

(73) Assignee: Marfly 1, LP, St. Louis, MO (US)

( * ) Notice: Subject to any disclaimer, the term of this patent is extended or adjusted under 35 U.S.C. 154(b) by 2256 days.

(21) Appl. No.: 10/729,082

(22) Filed: Dec. 5, 2003

(65) Prior Publication Data

US 2004/0117215 A1    Jun. 17, 2004

Related U.S. Application Data

(63) Continuation-in-part of application No. 10/253,194, filed on Sep. 24, 2002, which is a continuation-in-part of application No. 09/910,190, filed on Jul. 19, 2001, now Pat. No. 7,698,154.

(60) Provisional application No. 60/219,773, filed on Jul. 20, 2000.

(51) Int. Cl.
  *G06F 19/00*   (2011.01)
  *G06K 17/00*   (2006.01)
  *A61B 5/02*    (2006.01)
  *G06Q 50/24*   (2012.01)

(52) U.S. Cl.
  CPC .............. *G06F 19/322* (2013.01); *G06Q 50/24* (2013.01); *G06F 19/328* (2013.01)
  USPC .................................................. 705/3; 705/2

(58) Field of Classification Search
  USPC ........................................................ 705/3
  See application file for complete search history.

(56) References Cited

U.S. PATENT DOCUMENTS

| | | |
|---|---|---|
| 3,872,448 A | 3/1975 | Mitchell, Jr. |
| 4,130,881 A | 12/1978 | Haessler et al. |
| 4,315,309 A | 2/1982 | Coli |
| 5,065,315 A | 11/1991 | Garcia |
| 5,099,424 A | 3/1992 | Schneiderman |
| 5,277,188 A | 1/1994 | Selker |
| 5,510,832 A | 4/1996 | Garcia |
| 5,553,609 A | 9/1996 | Chen et al. |
| 5,572,421 A | 11/1996 | Altman et al. |
| 5,619,991 A | 4/1997 | Sloane |
| 5,633,910 A | 5/1997 | Cohen |
| 5,704,371 A | 1/1998 | Shepard |

(Continued)

OTHER PUBLICATIONS

Office Action issued in U.S. Appl. No. 09/910,190; dated Nov. 16, 2007; 33 pages.

(Continued)

*Primary Examiner* — Hiep V Nguyen
(74) *Attorney, Agent, or Firm* — Senniger Powers LLP

(57) ABSTRACT

A system and process for providing a computerized medical and biographical records database and diagnostic information. A medical records database and diagnostic program is stored on a central computer that is accessible to individuals using remotely situated computers connected to a computer network. Individual patient medical and biographical records are owned by individual patients who can enter information in their record as well as grant or deny authorization to others, such as health care professionals, insurance providers and other entities, to review part or all of their record. The method, process and system establishes the parameters of function of providers and users of the services, stores all available data, provides the functional platforms for all medical, non-medical, and financial transactions to occur in an electronic, software-guided, anonymous, efficient, and uniform environment.

37 Claims, 11 Drawing Sheets

(56) References Cited

U.S. PATENT DOCUMENTS

| | | | |
|---|---|---|---|
| 5,732,397 | A | 3/1998 | DeTore et al. |
| 5,764,774 | A | 6/1998 | Liu |
| 5,772,585 | A * | 6/1998 | Lavin et al. ............... 600/300 |
| 5,823,948 | A | 10/1998 | Ross, Jr. et al. |
| 5,832,450 | A | 11/1998 | Myers et al. |
| 5,839,438 | A | 11/1998 | Graettinger et al. |
| 5,845,253 | A | 12/1998 | Rensimer et al. |
| 5,910,107 | A | 6/1999 | Iliff |
| 5,911,132 | A | 6/1999 | Sloane |
| 5,924,074 | A * | 7/1999 | Evans ............... 705/3 |
| 5,935,060 | A | 8/1999 | Iliff |
| 6,026,363 | A * | 2/2000 | Shepard ............... 705/3 |
| 6,039,688 | A | 3/2000 | Douglas et al. |
| 6,149,440 | A | 11/2000 | Clark et al. |
| 6,234,964 | B1 | 5/2001 | Iliff |
| 6,260,021 | B1 | 7/2001 | Wong et al. |
| 6,263,330 | B1 | 7/2001 | Bessette |
| 6,463,417 | B1 | 10/2002 | Schoenberg |
| 6,523,009 | B1 | 2/2003 | Wilkins |
| 6,694,042 | B2 * | 2/2004 | Seder et al. ............... 382/100 |
| 6,849,045 | B2 | 2/2005 | Iliff |
| 6,874,085 | B1 | 3/2005 | Koo et al. |
| 6,941,271 | B1 | 9/2005 | Soong |
| 6,988,075 | B1 * | 1/2006 | Hacker ............... 705/3 |
| 7,295,988 | B1 * | 11/2007 | Reeves ............... 705/3 |
| 7,593,952 | B2 * | 9/2009 | Soll et al. ............... 1/1 |
| 2001/0032100 | A1 * | 10/2001 | Mahmud et al. ............... 705/2 |
| 2001/0041991 | A1 * | 11/2001 | Segal et al. ............... 705/3 |
| 2002/0046346 | A1 | 4/2002 | Evans |
| 2002/0049614 | A1 * | 4/2002 | Rice et al. ............... 705/3 |
| 2002/0062225 | A1 | 5/2002 | Siperco |
| 2005/0060197 | A1 | 3/2005 | Mayaud |
| 2005/0165626 | A1 | 7/2005 | Karpf |
| 2005/0172022 | A1 | 8/2005 | Brown |

OTHER PUBLICATIONS

Anand et al., "Watermarking Medical Images with Patient Information," Proceedings of the 20th Annual International Conference of the IEEE Engineering in Medicine and Biology Society, 1998, pp. 703-706, vol. 20.

* cited by examiner

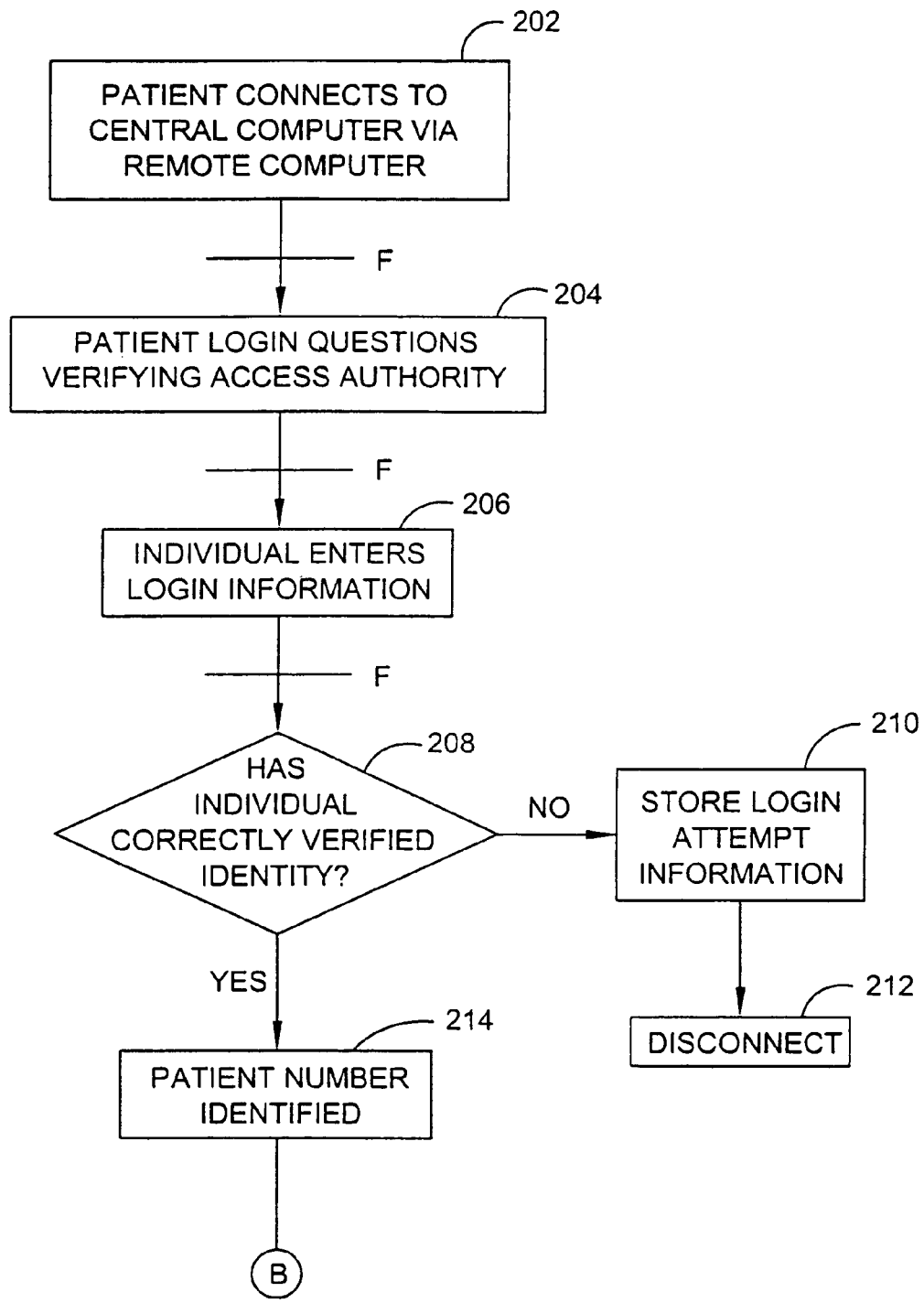

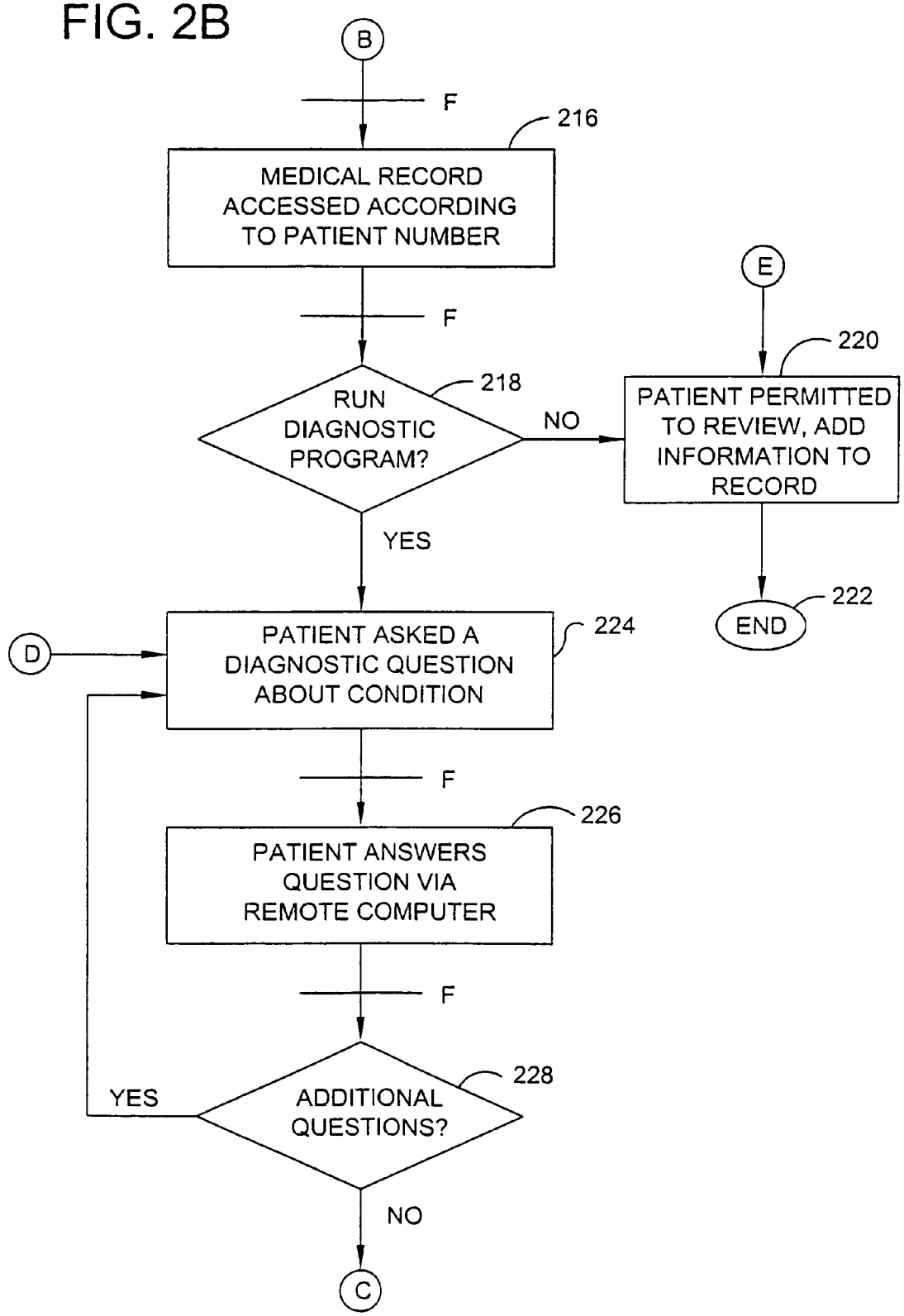

FIG. 3

Diagnostic Answer Weighting Values

| Answer Weighting Value | Frequency (preferred categorization) | Frequency |
|---|---|---|
| -10 | Impossible to be connected to diagnosis | |
| -9 | Extreme contraindication for diagnosis | Very strong indication for different diagnosis |
| -8 | Very Strong contraindication for diagnosis | |
| -7 | Strong contraindication for diagnosis | Strong indication for different diagnosis |
| -6 | Definite contraindication for diagnosis | |
| -5 | Contraindication for diagnosis | Indication for different diagnosis |
| -4 | Extremely unlikely to occur with diagnosis | |
| -3 | Very unlikely to occur with diagnosis | Potential indication for different diagnosis |
| -2 | Strongly unlikely to occur with diagnosis | |
| -1 | Unlikely to occur with diagnosis | Extremely unusual |
| 0 | Extremely rare or irrelevant to disease diagnosis | |
| 1 | Rare | Unusual |
| 2 | Infrequent | |
| 3 | Occasional | Below average |
| 4 | Often | |
| 5 | Common | Average |
| 6 | Frequent | |
| 7 | Important | Strong |
| 8 | Very important | |
| 9 | Extremely important | Very Strong |
| 10 | Indispensable | |

FIG. 5

| 502 | 504 | 506 | 508 | 510 | 512 | 514 | 516 |
|---|---|---|---|---|---|---|---|
| SYMPTOMS | CODE* | ANSWER | ANGINA | MYOCARDIAL INFARCTION | PULMONARY EMBOLUS | CARTOID ARTERY DISSECTION | PNEUMONIA |
| PAIN | | | | | | | |
| CHEST | 000001 | 111 | 10 | 10 | 10 | 8 | 5 |
| ABDOMEN | 030001 | 000 | 0 | 0 | 0 | 0 | 0 |
| BACK | 295001 | 000 | 0 | 0 | 0 | -3 | 0 |
| SHOULDER | 380001 | 111 | 8 | 10 | 4 | 0 | 3 |
| FLANK | 330001 | 000 | 0 | 0 | 0 | 0 | 0 |
| JAW | 115001 | 111 | 6 | 10 | 0 | 0 | 0 |
| NECK | 380200 | 111 | 6 | 10 | 0 | 0 | 0 |
| AXILLA | 380300 | 000 | 0 | 0 | 0 | 0 | 0 |
| OTHER SYMPTOMS | | | | | | | |
| DIAPHORESIS | 001010 | 111 | 8 | 10 | 4 | 2 | 8 |
| NAUSEA | 085010 | 111 | 8 | 10 | 4 | 2 | -6 |
| TOTALS | | | 256 | 285 | 170 | 111 | 27 |

* FIVE LEADING ZEROS OF CODE NOT SHOWN DUE TO SPACE CONSTRAINTS.

518 → CHEST
520 → ABDOMEN
522 → BACK
524 → TOTALS

RECORD SYSTEM

CROSS-REFERENCE TO RELATED APPLICATION

This application is a continuation-in-part of U.S. patent application Ser. No. 10/253,194 filed Sep. 24, 2002, which is a continuation-in-part of U.S. patent application Ser. No. 09/910,190 filed Jul. 19, 2001, now issued as U.S. Pat. No. 7,698,154 on Apr. 13, 2010, which claims priority from U.S. Provisional Patent Application Ser. No. 60/219,773 filed Jul. 20, 2000, all of which are hereby incorporated by reference.

BACKGROUND OF THE INVENTION

The present invention generally relates to a method and system of managing medical and biographical records and providing medical diagnoses.

Patient medical and biographical records and medical diagnostic software are stored on a centralized computer accessible by remotely connected computers. The medical records are essentially "owned" by an individual patient who grants or denies varying degrees of access to the records to selected health care professionals based on the health care professional's field of specialty and need to know. The medical diagnostic software receives information provided by the patient and provides the patient with a list of potential medical diagnoses. This information also forms part of the patient's medical record.

Medical record systems are well known in the prior art. Medical records have been used throughout the years of the practice of medicine in order to keep track of a patient's medical history, medical observations, diagnoses and any treatments prescribed to the patient. Often, a record contains information as to the success or failure of a particular treatment, a patient's allergies and reactions to drugs or treatments, and a record of patient visits. In addition to serving as a record of medical history and treatment, the medical record also serves as legal documentation of patient condition and treatment.

Evolution of the health care system is engendering reevaluation of the roles of patients and health care providers with regard to access and content of medical records. Long term relationships and trust between a family doctor and patient are no longer commonplace because changes in residence, job, or insurance carrier often require the patient to change primary and/or specialty health care providers. Establishing relationships with a new health care provider can be tedious as medical records must first be transferred from previous health care providers and then reviewed by the new health care provider for past history, therapies, and present therapeutic regimes. Also, the new medical record being created by the new health care provider is often incomplete as patients frequently fail to remember to include all the necessary medical or biographical information. In fact, patients sometimes convey erroneous information that can be ultimately detrimental to their health.

Control of the information contained in a patient's medical and biographical record is also becoming a significant public issue. Presently, such records are treated as being "owned" by the medical offices or institutions in which the records are housed. Distrust on maintenance of confidentiality results in failure to disclose information that may be important for health-care decisions. This distrust may be increased as patients transfer to new health care providers.

Medical record systems usually consist of handwritten notes, pictures, and documents created by a medical and health care provider. Recently, computer programs and systems have become available for the generation, storage, and retrieval of medical records. In general, such systems operate on a computer owned by a hospital or other health care provider and may only be accessed by health care professionals affiliated with the health care provider. Patient medical information is typically input into a medical record by a physician, nurse, or other health care professional.

Several automated medical record systems have been designed and marketed in the health care field. For example, U.S. Pat. No. 5,277,188 discloses a clinical information reporting system having an electronic database including electrocardiograph related patient data. Similarly, U.S. Pat. No. 5,099,424 discloses a computer system for recording electrocardiograph and/or chest x-ray test results for patients. U.S. Pat. No. 4,315,309 discloses a patient report generating system for receiving, storing and reporting medical test data for a patient population. U.S. Pat. No. 3,872,448 likewise discloses a system for automatically handling and processing hospital data, such as patient information and pathological test information using a central processing apparatus. In U.S. Pat. No. 5,065,315, a computerized scheduling and reporting system is disclosed for managing information pertinent to a patient's stay in the hospital. Also, U.S. Pat. No. 5,924,074 discloses an electronic data processing system.

While present automated systems may provide electronic storage of medical data, they typically suffer from significant shortcomings that have plagued medical record systems since their inception. These systems, like their paper record counterparts, are typically only available to health care professionals affiliated with the hospital, clinic, or other health care provider that owns the medical record software program and computer system. Thus, the information contained in a patient's medical record would not be reviewable by another health care professional who is not affiliated with the health care provider that maintains the medical record software. This becomes an issue for patients who choose to be treated by a different health care provider or who may require treatment while traveling in a location not served by their usual health care provider. Treatment may be prescribed which has been previously determined to be ineffective or which is contraindicated for the patient.

Similarly, health care professionals from different health care providers may not be able to easily review a patient's medical record and confer with each other as to diagnosis and treatment. This may be due to either security controls by the health care provider or by incompatible systems used by different health care professionals. Thus, health care professionals wishing to confer with each other may be required to copy and mail or send a facsimile of the patient's record, introducing privacy and control issues.

Since the existing systems are "owned" by the health care provider, a patient may be kept from reviewing his or her own medical record for the substance or accuracy of its information. Additionally, a patient cannot prevent or control private information contained within the patient's medical record from being seen by any individual that has access to medical records, regardless of whether the individual has any right or need to review a particular portion of the patient's medical record. As such, information which the patient wishes to remain private may be reviewed, thereby compromising the patient's privacy and potentially introducing a negative bias to the health care professional towards the patient. An example of such information may include past treatment for a sexually transmitted disease or sexual dysfunction that may be irrelevant to a particular medical specialty.

Current medical systems also often do not contain useful data such as family history, biographical data, genetic constitution or make-up, or other information that a patient may add to his or her medical record which could aid health care professionals in diagnosing the patient's condition or determine the best medical treatment.

Moreover, presently available medical records systems are not suited for providing medical diagnoses. Advancements in automation, research, specialization and medical knowledge have permitted modern day health care to be increasingly improved over the care provided in the recent past. While these advancements have resulted in improved success rates of medical treatment, individuals often delay seeking medical attention due to fear of the unknown and the inconvenience of being referred to multiple physicians. Patient referrals typically occur when a primary care physician makes a general diagnosis, then refers a patient to a physician specializing in the area of the diagnosis. Further referrals may occur if the patient is referred to medical sub-specialties for further diagnosis and treatment resulting in additional patient cost, time, and inconvenience. Patients who face these inconveniences and costs or who have experienced them in the past may delay seeking treatment in the hope that a condition may simply go away thereby precluding the need to seek the help of a health care professional. This delay can cause a medical condition which could be easily treated early in its development to require longer treatment or the condition may even become untreatable by the time medical assistance is sought. If the same patients were informed of potential diagnoses of their conditions, they can be aware of the risks of delaying medical assistance and may be persuaded to seek help earlier. Informed patients may even be able to reduce the inconveniences of multiple referrals by initially seeking the assistance of a health care professional who specializes in treating their particular condition.

Medical information is readily attainable to the public through medical books available in libraries and bookstores, medical phone help or "Ask-A-Nurse" telephone services, audio visual informational programs on television and videotape, and Internet sites specializing in medical care such as "WebMD.com". The amount of available information, however, can be overwhelming to an individual trying to determine the identification of his or her particular health condition who is unfamiliar with researching health information or who lacks a scientific background.

Computer programs have been developed to provide individuals potential diagnoses based on their responses to a series of health-related questions. U.S. Pat. Nos. 5,910,107 and 5,935,060, for example, describe diagnostic programs which can be accessed over a telephone or computer network. An individual is asked a series of weighted questions concerning the individual's health symptoms and can respond with "yes," "no," or "not sure" answers or may be asked to answer multiple-choice questions. From the responses, the program identifies a list of potential diseases which are indicated by the individual's health symptoms. U.S. Pat. No. 5,572,421 discloses an electronic medical history questionnaire in which a patient can respond "yes," "no," or "not sure" to medical questions. The questionnaire then provides the physician with suggested tests that may be performed and conclusions regarding the patient's health. U.S. Pat. No. 5,839,438 discloses a diagnostic system using a neural network to provide a patient diagnosis to a physician from input data comprising measured and interview data regarding the patient's condition. The diagnosis is based upon a databases of physician diagnoses of medical conditions and their corresponding symptoms.

While prior art automated medical diagnostic programs diagnose a condition or confirm a diagnosis made by the physician, they are usually designed to be used by a physician and not a patient. The language and phrasing in these programs are designed for a health care professional and contain esoteric medical and health terms. Most patients do not understand these terms and therefore cannot effectively use the programs. Thus, the diagnostic information provided by these programs does not inform individuals of their various conditions before they seek medical assistance. A further shortcoming of prior art automated diagnostic programs is that they can accept input data that is often erroneous or not helpful. As an individual may select "not sure" or other answers which are not simply "yes" or "no," an individual is able to avoid answering conditions they feel are minor are irrelevant, but which may provide helpful data if the individual were forced to select only a "yes" or "no" response. Thus a software program designed to accept objective data and provide individuals with diagnostic information about their health conditions would be desirable.

Accordingly, it would be beneficial to patients and health care professionals alike to develop an individual patient self-generated, fully controlled and censored, centralized electronic medical and biographical records and medical diagnostic system that may be accessed by patients and health care professionals regardless of their affiliation with a particular hospital, clinic, or other health care provider. The medical and biographical records and medical diagnostic system would be maintained, stored and delivered by a totally independent institution, not necessarily affiliated with the government, insurance or health care industry. By using common language and phrasing tailored to different levels of education and familiarity with medical and health terms an individual could effectively utilize such a system to determine potential diagnoses prior to seeking medical attention, permit the individual to be better informed as to the potential medical specialty from which to seek assistance, and control the content of and access to the individual's medical record.

A self-generated record of present illness and pertinent information would also benefit individuals by allowing them ample opportunity to ponder and respond without encumbrances from health care providers presence. Such presence often generates discomfort or uneasiness and may lead to confused, unconsciously withheld, consciously suppressed information (e.g., suppressed for fear of embarrassment) or miscommunicated medical and biographical information.

A centralized electronic medical and biographical records and medical diagnostic system would also permit any health care professional to be aware of all of a patient's biographical and medical history that is relevant to treating the patient. Additionally, since the centralized medical and biographical records system would not be the property of any one health care provider, the individual medical records could be owned by individual patients. Thus, patients may authorize or deny access to their medical and biographical records or limit access to only portions of their medical record to specific health care professionals thereby controlling privacy of the patient and confidentiality of the patient's medical and biographical information. Patients also benefit by being able to add biographical information about themselves as well as review and comment on the contents of their records input by others for substance and accuracy.

A centralized electronic medical and biographical records and medical diagnostic system would also be beneficial in reducing health care costs and being a foundation upon which health care insurance programs may be based. By centralizing the medical history of a patient, reduced costs may be realized through avoiding repeating tests or prescribing medications or treatment that has been previously found to be unsuccessful or contraindicated. Therefore, by reducing unnecessary treatment, health costs would be reduced, resulting in lower insurance premiums from insurers that would not have to cover unnecessary treatments.

Many health care providers and insurance carriers have vast archives of documents that are critical from both historical and operational perspectives. Accordingly, these documents should be incorporated into the medical and biographical records of the patients. At present, the cost of incorporating these documents is prohibitive due to the need for human intervention during document indexing. Further, document recognition and indexing is subject to error when performed by humans. Thus, there is a need for an automated method of document recognition and indexing.

SUMMARY OF THE INVENTION

Briefly, the present invention includes a medical records system comprising a central computer connected to a global computer network having a medical records database thereon. The database contains individual medical records of a plurality of patients. Each of the records corresponds to one patient of the plurality of patients. The system further comprises a patient computer connected to the global network remote from the central computer having a patient interface program adapted to permit a patient to input medical history and biographical information into the medical records database and to authorize a health care professional to access at least a portion of the individual medical records of the respective patient. In addition, the system comprises a health care computer connected to the global network remote from the central computer having a health care professional interface program adapted to permit an authorized health care professional to access the portion of the individual medical records and to input additional patient medical history and biographical information into the corresponding individual medical record of the database.

In another aspect, the present invention includes a method for providing health care services to a plurality of patients. The method comprises acquiring individual medical records from each patient within the plurality of patients, and storing the records in a database on a central computer. Each of the records corresponds to a particular patient. The storing is performed only upon approval of the particular patient. The method further comprises permitting a health care professional to access a specific record in the database corresponding to the particular patient based on approval from the particular patient.

In still another aspect, the present invention includes a method for providing health care services to a plurality of patients comprising establishing rules for delivering and receiving health care services, and acquiring individual medical records from each patient of the plurality of patients. In addition, the method includes requiring a particular patient of the plurality of patients to update the medical record by inputting current information, and storing the records obtained from the particular patient in a database on a central computer. Further, the method includes requiring authorization from the particular patient to grant a health care professional access to at least a portion of the corresponding individual medical record of that particular patient prior to receiving health care services from the health care professional. Still further, the method comprises requiring the authorized health care professional to review the portion of the record in the database corresponding to the particular patient prior to the rendering of health care services, and requiring the authorized health care professional to provide an accurate record of the health care services rendered.

In yet another aspect, the invention includes a method for delivering health care while controlling interaction between users, providers and payers through parameters and rules comprising determining health care service user eligibility, determining health care service provider eligibility, and establishing rules for the administration of the health care service system. Further, the method includes determining reasonable costs for health care products and services, and determining health care services that will be paid by the administrator or a third party. In addition, the method comprises dispersing payment to health care service providers, ensuring availability of health care services, eliminating unnecessary use and abuse of health care services, guiding development of future services, monitoring health care service users' compliance with established rules of the health care service system, monitoring health care service providers' compliance with established rules of the health care system, and enforcing all rules of the health care service system.

In another aspect, the invention includes a health care process comprising inputting pertinent and accurate medical and biographical data into a health care service user-controlled electronic medical records database, seeking health care services only when necessary, authorizing certain health care service providers access to applicable information in their biographical and medical records database, using the provided services, products, therapies or treatments as prescribed by the health care service provider, reviewing data inputted by any health care service provider into the biographical and medical records database for accuracy, and reporting any inaccuracies in the data inputted by the health care service provider.

Other features of this invention will be in part apparent and in part pointed out hereinafter.

BRIEF DESCRIPTION OF THE DRAWINGS

FIG. 3 illustrates exemplary relative weighting values assigned to answers of diagnostic questions for a given medical condition based on the likelihood that a given answer is related to a potential diagnosis.

FIG. 5 illustrates exemplary diagnostic questions and their correlation to, diagnostic codes, patient answers to diagnostic questions, and the value weighting of the answer corresponding to different diseases according to the invention.

Corresponding reference characters indicate corresponding parts throughout the several views of the drawings.

DETAILED DESCRIPTION OF EMBODIMENTS

Figure 1:
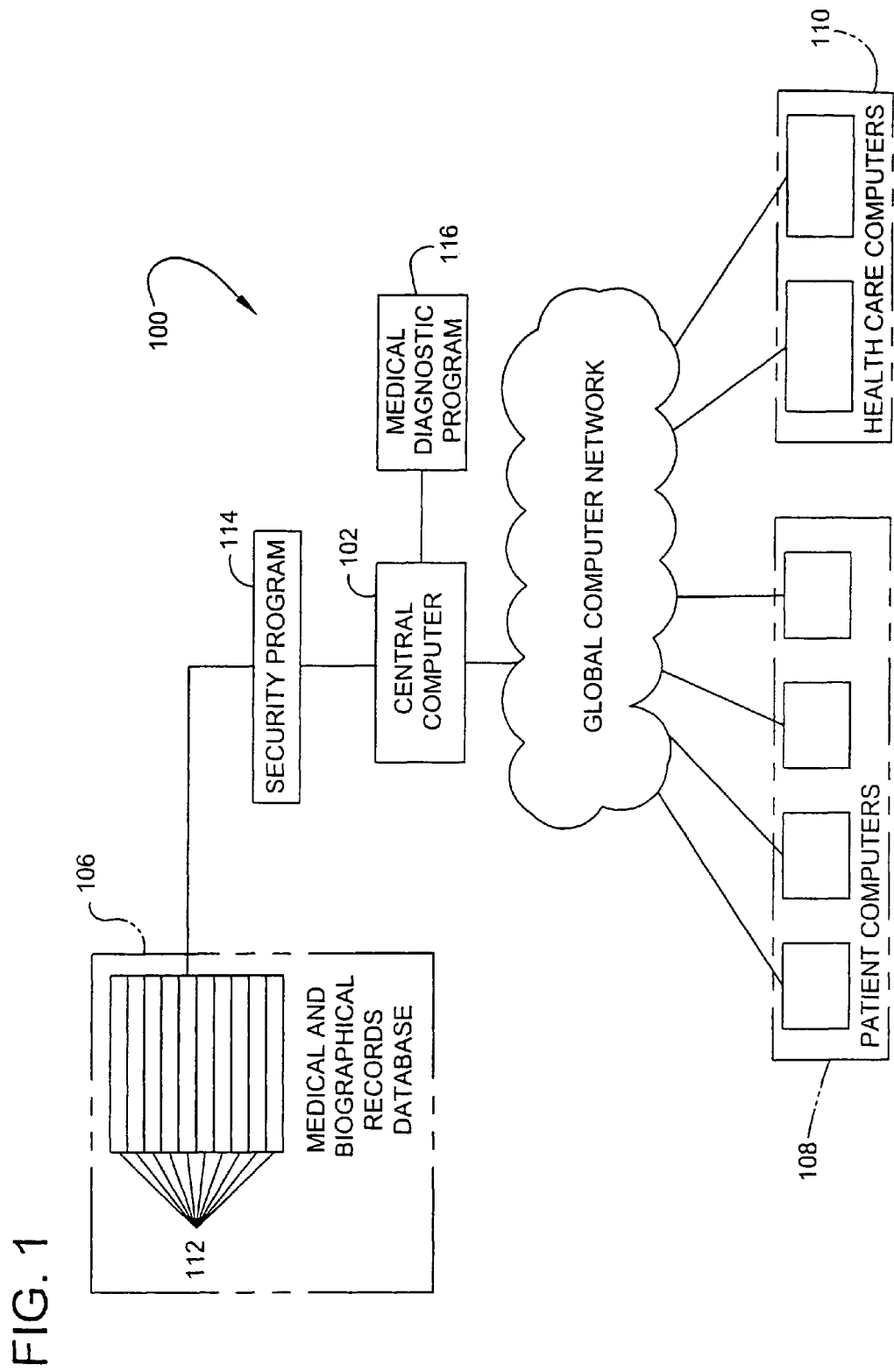
FIG. 1 is a block diagram of a computer system according to a preferred embodiment of the invention.

Referring now to the drawings, FIG. 1 is an illustrative embodiment of the present invention, which relates to automated medical and biographical and diagnostic systems. Particularly, the invention relates to a voluntary system, shown generally at 100, in which an individual patient's medical and biographical record information can be accessed, added, modified, maintained, and controlled by the patient. Furthermore, system 100 provides medical diagnostic information in which the patient obtains a list of potential medical diagnoses corresponding to input health symptoms.

The present invention includes a central computer 102 connected to a global computer network 104 (e.g., the Internet or a private intranet). Central computer 102 also has access to a medical and biographical records database 106 containing a plurality of medical and biographical records 112 for individual patients. A plurality of patient computers 108 and health care computers 110 are also connected to global computer network 104.

Patients obtain access to their medical and biographical records by accessing central computer 102 via patient computers 108 connected to global computer network 104. Central computer 102 executes a security program 114 that limits access to medical and biographical database 106 and individual medical and biographical records 112 contained therein. Once a patient's identity is verified by security program 114, the patient access his or her own individual medical and biographical record 112.

Similarly, health care providers obtain access to patients' medical and biographical records by accessing central computer 102 via health care computers 110 connected to global computer network 104. Central computer 102 executes security program 114 to limit access to medical and biographical database 106 and individual medical and biographical records 112 contained therein to health care providers who are authorized by a patient to access the particular patient's medical and biographical record 112.

Additionally, individuals, whether patients, health care providers, or simply individuals interested in inquiring about a health condition, may execute medical diagnostic program 116 by accessing central computer 102 via either patient computers 108 or health care computers 110 connected to global computer network 104. Results from the execution of medical diagnostic program 116 are provided by central computer 102 to either patient computers 108 or health care computers 110 via global computer network 104.

The creation and maintenance of medical records, including: recording and correlating past medical history and biographical information; integrating genetic, laboratory, radiological, and imaging results, prescribed medications, and treatments; noting patient allergies, reactions, and treatment outcome; updating medical records; emergency recalling medical records; and making medical records available and transportable is a very detailed and involved task. Extreme care is required to preserve and protect all the information contained in medical records as well as ensure that authorized personnel are able to retrieve information when it is requested. The task is complicated because of the difficulty in obtaining, maintaining, and correlating the information as well as providing security measures to protect access to the information. Solving these multiple difficulties while organizing the system to provide a user friendly program provides substantial benefits to patients and health care professionals.

With the extensive and rapidly increasing pharmaceutical armamentarium available today, it has become difficult for health care providers and patients to be aware of all the drugs taken in the past and the present, as well as their generic equivalents, interactions, and side effects. This situation is further compounded by the increasing inclusion of over-the-counter drugs, herbal treatments, and the like that many patients intake regularly but do not consider as part of their "medicines" and therefore neglect to inform their health care providers that they are taking such substances. By providing a central registry and a rapid individualized analysis and correlation system, prompt warnings regarding interactions, side effects, and previous use (including effectiveness or lack of efficacy), can be extremely useful and beneficial. Another important contribution of a central registry is the ability to differentiate between intolerance, side effects, or true allergies of patients to drugs.

Moreover, with the ever-increasing mobility of patients and families, the breakdown of roots and family connections, and advances in science, ready access to extensive knowledge of a patient's genealogy, genetics, environmental and biologic events become important and sometimes crucial in the differential diagnoses and therapy. For example, knowing the genealogy and place of origin of a patient may facilitate locating someone with similar genetic makeup for organ or tissue acquisition or transplantation (i.e., stem cells, etc.). Another example would be an environmental exposure, discovered many years after the event and its correlation to diseases or conditions, that appear unrelated until the correlation is made between biography, location and exposure.

For the patient, the benefits include (1) ready availability of a chronological register of a patient's lifelong medical history, (2) full control of access to personal information, (3) the ability to restrict personal facts or areas of information, (4) ready availability of an electronic, easily accessed, confidential, personal medical consultant for health condition diagnosis, (5) a potential reduction in the need for medical services thereby saving money and inconvenience, (6) protection from conflicting therapies, (7) unbiased health care and insurance referral service, and (8) portability of medical history and biographical information between health care providers.

System 100 includes medical and biographical records database 106 containing medical and biographical records 112. The patients, being the owner of their own folios, are able to review what is in their folios. They also control access to their folios in part or in total. For example, a female patient may provide a family doctor with authorization to access general health information in her folio but prevent her family doctor from accessing information she permits only her gynecologist to review.

While the present invention contains medical and biographical records 112 that are the property of individual patients, it may also contain medical records and biographical records 112 that are owned by individual health care providers such as doctors, clinics, hospitals, and the like. A health care provider may archive some or all of its own records on system 100 and benefit from its central access, security provisions, and other features. In contrast to a folio of an individual patient, the health care provider's archive may contain folios of numerous individual patients that receive treatment from the heath care provider.

Patients and health care providers may add both medical and biographical patient information such as physical examinations, genetic constitution and history, social history, mental and emotional health history, organ system history, surgical history, environmental history, dental and oral health history, laboratory results, radiological and imaging history, treatment therapies and medications history, otologic and ophthalmologic history, past history of prior injuries, patient health related events, job related health issues, chemical exposures, temperature, metabolic profiles, organ function tests, biochemical, anatomical, physiological, and pathological histories, alternative medicines, and so forth. Entered information may also include family history, or any other information the patient desires to be contained in his or her folio. Additionally, the patients may review entries made by their health care professionals. While the patients cannot delete authorized entries by health care professionals, they may add comments they feel are necessary to clarify an entry.

As described above, the folios are stored as records 112 in database 106 associated with central computer 102. Central computer 102 is connected to a computer network, preferably global computer network 104. Patients and the people they authorize are able to access a patient's folio remotely from central computer 102 via computers 108 connected to computer network 104. A significant benefit of the present invention is the ability of patients, and the people who they authorize, to access medical and biographical information stored in a patient's folio regardless of the affiliation of the patient or the health care professional to a particular clinic, hospital or other health care provider. This is significant because a patient's folio may be accessed regardless of whether he or she is being treated at a local health care provider or a remote health care provider such as when a patient is injured while traveling or on vacation.

The present invention can also be modified to provide information in different languages and to translate information from one language to another. Thus, for example, English language text and information can be translated to Spanish to permit Spanish-speaking individuals to effectively use the system.

Another benefit of the present invention is the ability to maintain a complete medical and biographical record over a patient's life. Medical records of the prior art are typically in varying states of completeness and reside at various health care providers who a patient has used over his or her lifetime. In contrast, the present invention provides a centralized medical and biographical record database, which could be used by all health care providers when treating the patient. As is well known, even the most interested and compulsive of people lack the discipline and perseverance to maintain a record of their lives. Many important pieces of data are forgotten, remembered inaccurately, or confused chronologically. Allowing long-term compilation of data facilitates chronological or correlative analysis which presently is mostly nonexistent. Thus, the patient's folio would be essentially complete and selectively accessible to any authorized physician, dentist, or other person.

In a preferred embodiment, each record 112 includes one or more sectors of related medical and biographical information. Although each sector preferably includes individual and independent units, system 100 provides correlative activity between parts of the individual and independent units in a controlled manner. Access to information in each unit is limited to authorized individuals while at the same time serving the needs of all the potential users of the system 100.

In addition to information contained in patient medical and biographical records 112, system 100 preferably provides information that is useful to both the patient and physician. Hyperlinks to scientific and medical sources, for example, medical information relating to health signs and symptoms, diagnostic references, medical and surgical therapies, and medical, pharmaceutical, and scientific dictionaries and thesauruses, are available in this embodiment for as much inquiry as desired. Hyperlinks can be designed to provide a progressive hierarchy to satisfy different levels of sophistication. Those skilled in the art understand there are many techniques for linking and searching via global computer network 104.

The present invention may include a variety of systems and processes to achieve an automated medical record, diagnosis, and treatment system and method that is patient owned and controlled. The following are examples of some systems and processes which may be included in the present invention: registration; identification; a security process and system to allow or deny accessibility to the medical and biographical records; entry of medical history; recording information in medical and biographical records (e.g., medical history; physical examination; anatomical, biochemical, physiological, pathological, and laboratory tests; and radiology and imaging information among other information); analysis and correlation of health symptoms; accessing disease and symptom oriented treatises such as the Merck Medical Manual, medical journals, and so forth; diagnosing medical conditions by weighting patient responses to diagnostic questions according to the relevancy of the answers to a particular disease or condition; providing an individual with therapeutic recommendations; recording actual medical therapies prescribed to a patient; predicting patient outcome to a given therapy; recording actual outcome to a given therapy; mental and emotional health and counseling; electronic dermatological evaluation which may include a dermatopathology atlas; electronic ophthalmologic evaluation and atlas; dental and oral care and surgery; providing an individual with social and welfare services; cumulative recording of radiological and imaging studies; cumulative recording and correlation of anatomical, biochemical, physiologic, pathologic, and laboratory studies; referral to health care provider; evaluating a health care provider; monitoring health care provider; notifying a patient of medical due dates; developing a genealogy tree; developing a patient's genetic constitution and history; providing access to medical, pharmaceutical, biologic, scientific dictionaries, thesauruses, etc.; acquisition and evaluation of audio and/or video information from directed self-examination; acquisition and evaluation of biologic parameters and electronic information and examinations; insurance program registration and automatic updating; and primary and specialist information interchange.

The preferred process and system requirements include immense data collection and correlation capability, easy portal accessibility, a multilevel security system, data entry and periodic upgrading by multiple health care providers; and acquisition of proprietary information and sources.

Referring now to the registration process, each patient will own his or her personal unique folio. System 100 permits only the patient, or his or her representative (e.g., parents of an underage child), to register. It is envisioned that eventually most patients will be registered at birth and the folio containing the patient's life medical history being maintained thenceforth. It is important to maintain a unique folio for each patient and to ensure that only the patient and those to whom the patient has granted authority will have access to the patient's folio. This may be done by requiring an identification sequence to be input wherein identifying data unique to the patient is required to access a folio. Examples of such identifying data include 1) full name of the patient without abbreviations, 2) state or country of birth, 3) birth date (dd/mm/yyyy), 4) patient social security number (SSN), and 5) a personal identification number (PIN). Additionally, as advances in technology permit, the identity of a patient may be verified by physical identifiers. Examples of such identifiers, also referred to as biometrics identifiers, include 1) fingerprint(s), 2) retinal or ocular image, 3) voice pattern (with or without a key verbal code), 4) DNA or genetic print, and 5) biochemical or blood type (AB, Rh, etc.).

In addition, depending on the level of security desired, an electronic signature may be required from the patient or registrant to enhance security of the identification sequence. The signature can be requested at the time of registration or at the end of the interaction to add further recognition of the validity of the included information, or as a legal validation of the preceding text. With the previously described registration and identification steps, the affixed signature at the end of the document, including the option of requiring repetition of the identification sequence, would improve the security of data as well as provide an electronic signature for legal purposes.

The identifying data references are keyed to a unique number randomly assigned to the patient upon initial registration. This number is randomly assigned to prevent a folio from being correlated to a particular registration date, patient name, or other information that may indirectly identify the identity of a particular patient. The unique number in turn references the patient's folio. Thus, the folio does not contain the actual patient identification data, but rather just the unique number. The separation of patient data from medical and biographical data and the requirement of a randomly assigned number increases the security of a patient's medical and biographical information from being accessed by an unauthorized individual breaking into computer 102 and its associated database 106 used to store the patient's folio. Thus, if unauthorized access is gained by someone breaking into system 100, all that could be accessed would be medical and biographical data that is anonymous except for the unique randomly assigned number.

By maintaining separation of a patient's identifying data from his or her actual medical and biographical data, medical and biographical data can be studied for information with full preservation of patient anonymity. This way longitudinal and population studies can be performed without compromising the confidentiality of a patient's medical and biographical record.

The PIN or biometric key permits the patient or an individual authorized by the patient to obtain access to the folio containing the patient's recorded medical and biographical data. Additional security procedures of the present invention may be implemented such as requiring reentry of the patient's PIN or biometric data when opening the folio or secured portions within the folio. Records copied without proper authority (i.e., without the patient's PIN or biometric verification) would be attached to a "cookie" that would eliminate or scramble the unauthorized copied data from any files where the data was copied. A "cookie" is a small program or file that executes a specific command, such as delete or scramble a file, executed on the computer into which the program has been imported.

In another embodiment, health care providers may also wish to take advantage of the security offered by the registration and identification sequence requirements provided by the present invention to store their patients' records. A health care provider may store multiple records of their patients. In this scenario, the identification sequence is the same as for any registrant, whether a health care provider or a patient. Once entered into the individual health care provider archive, access is granted to each one of the files the health care provider registrant has generated or stored in medical and biographical records database 106. The individual files contain only the information that the health care provider has specifically included in these files, but requires the active participation or an affirmative action of the health care provider for the inclusion of information to occur. This affirmative action confirms the positive desire for information inclusion, thereby negating possible health care provider assertion of ignorance of information inclusion. The system and method illustrated in FIGS. 1-5, described below, are the same for this embodiment except that the health care provider, and not the patient, controls access to the health care provider's patient records.

Access to each one of the patient records in the medical and biographical records database requires re-identification of the health care provider (by whichever measure is established by the health care provider) before opening the individual file. This additional step circumvents the possibility of unauthorized access to the files of the medical and biographical records database if it is inadvertently left open by the health care provider.

The system 100 further protects the health care provider's records or files from being forwarded to another file or database by requesting specific authorization for forwarding by the individual registered as the subject of the file. This extra measure complies with the requirements of the Health Insurance Portability and Accountability Act (HIPAA). The specific authorization restriction of HIPAA can be avoided by transferring the responsibility for the information to the individual, for the individual's personal files. The assumption is that all the health care information (excluding financial and other types of documents) contained in the health care provider files should be also included in the individual's personal file.

Figure 2C:
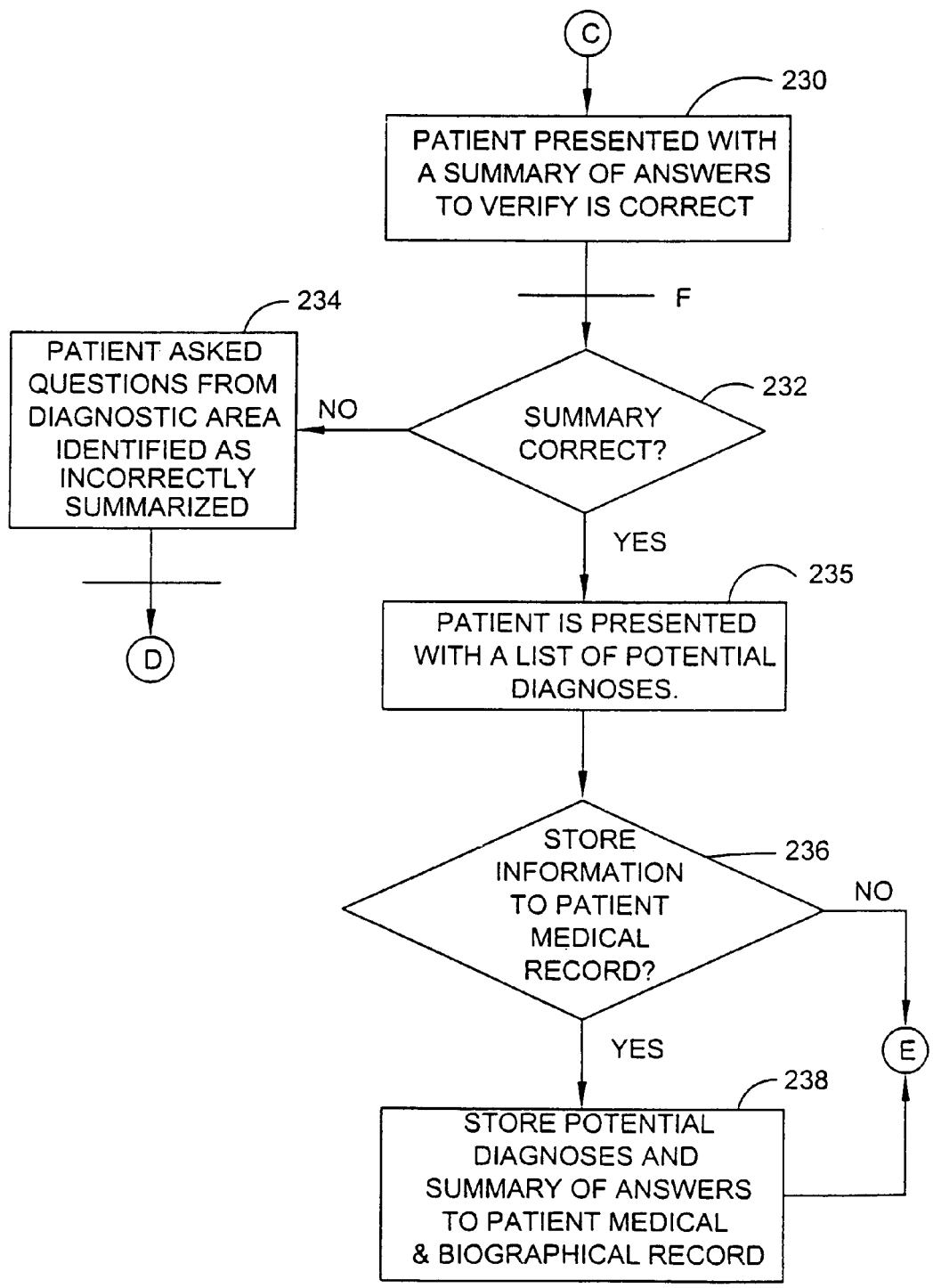
FIG. 2 is an exemplary flowchart illustrating a security program of the invention for verifying an individual's identity and authority to access a medical and biographical record.
Figure 4A:
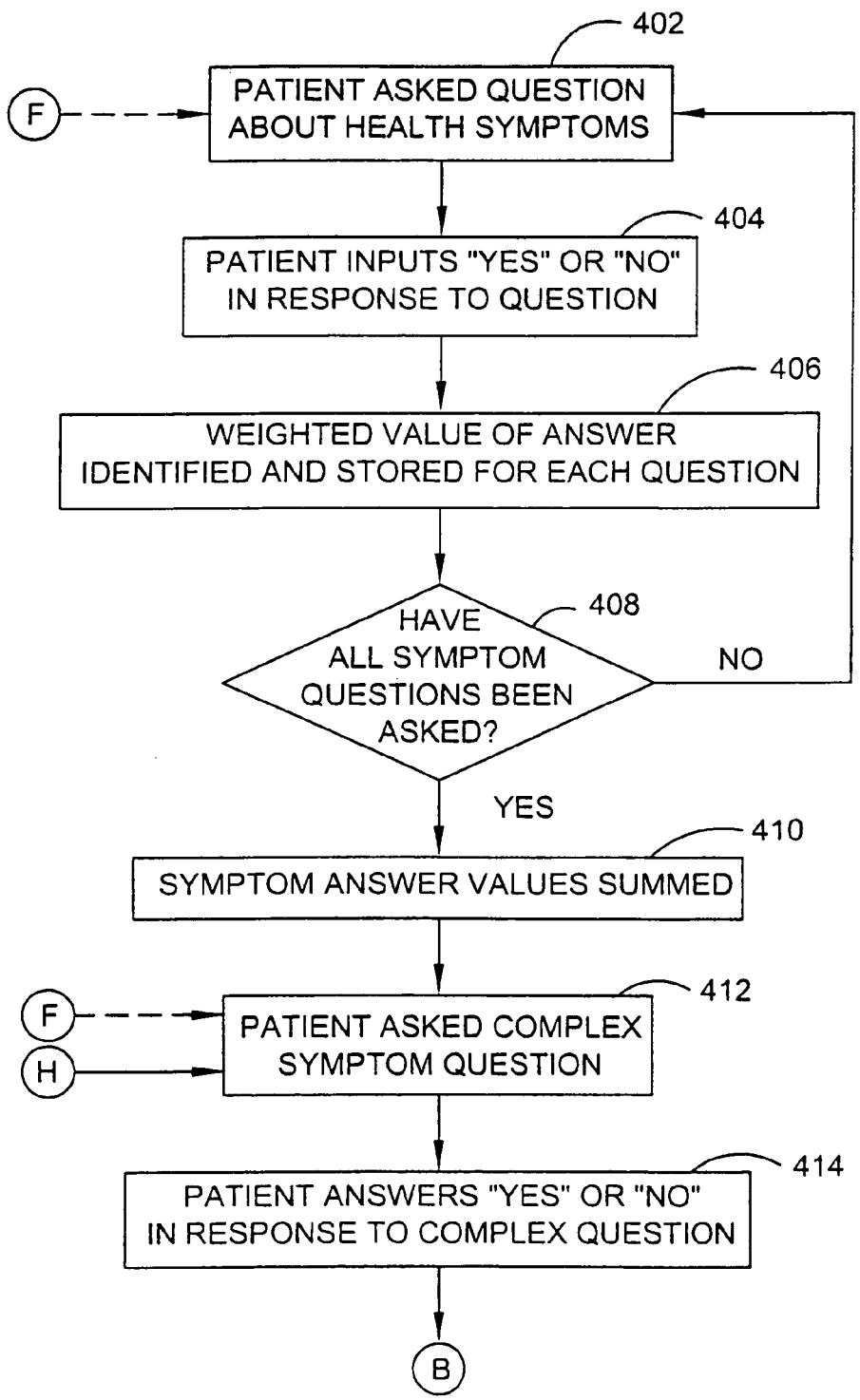
FIG. 4 is a flowchart of an exemplary medical diagnosis program according to the invention.
Figure 4B:
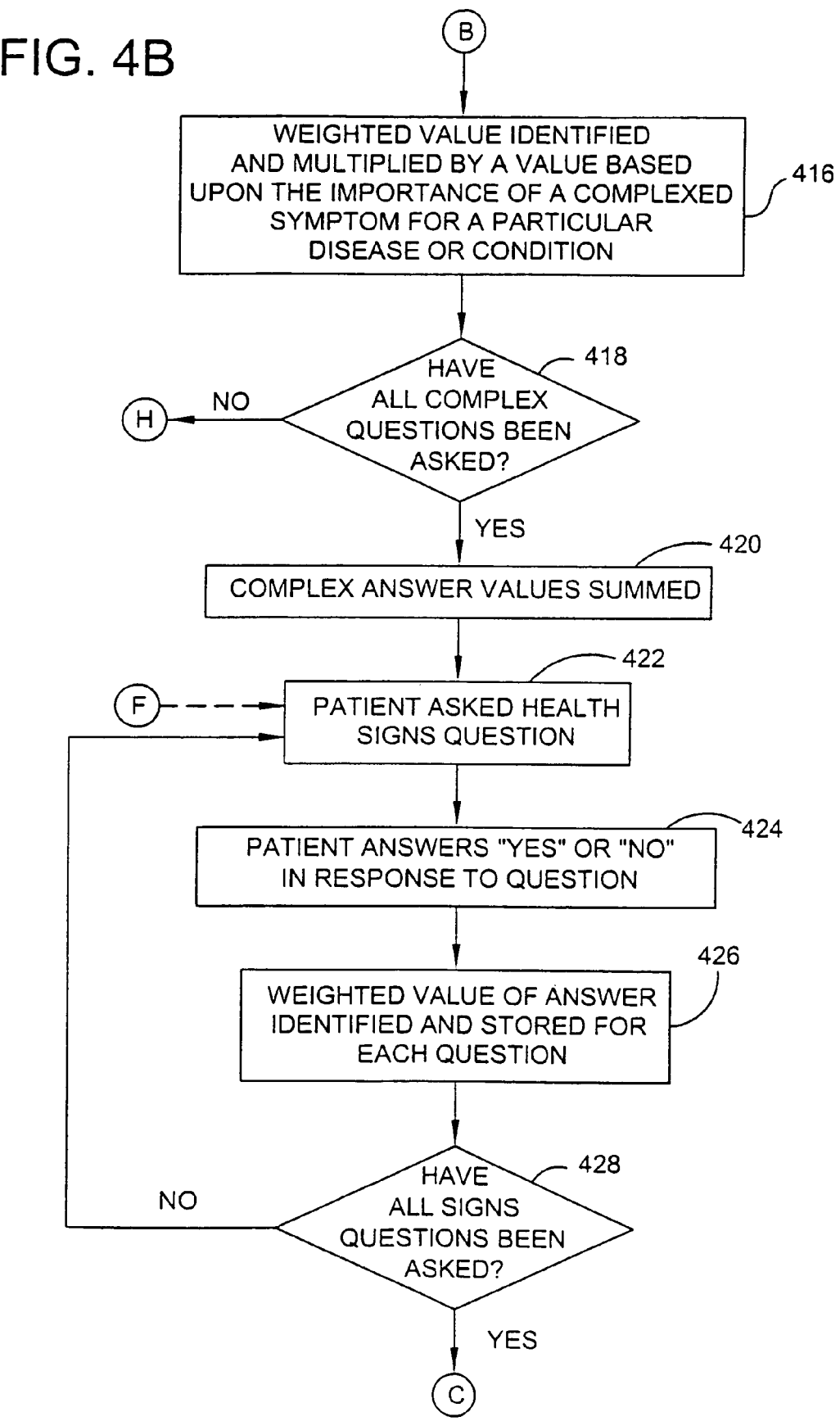
Figure 4C:
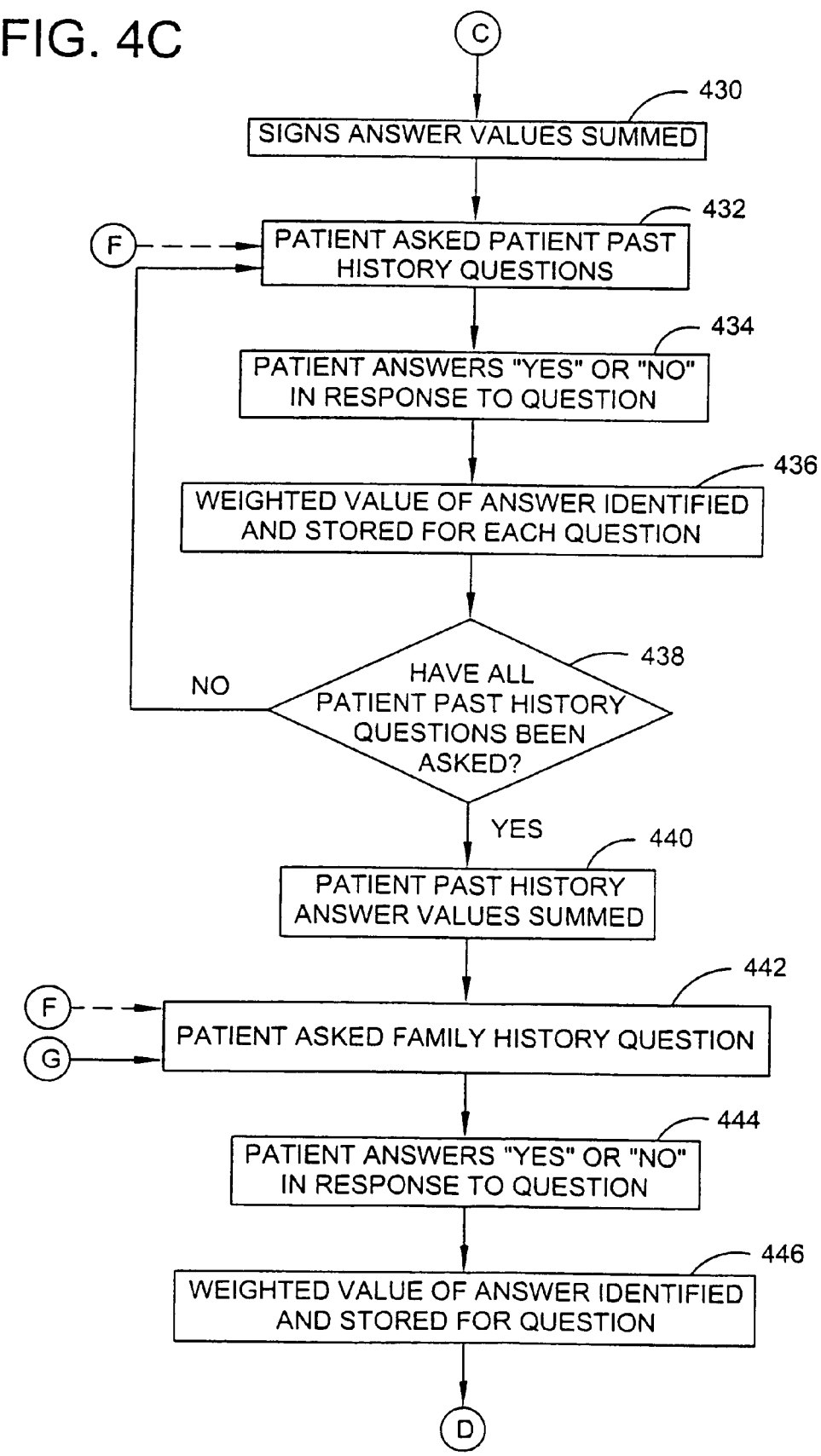
Figure 4D:
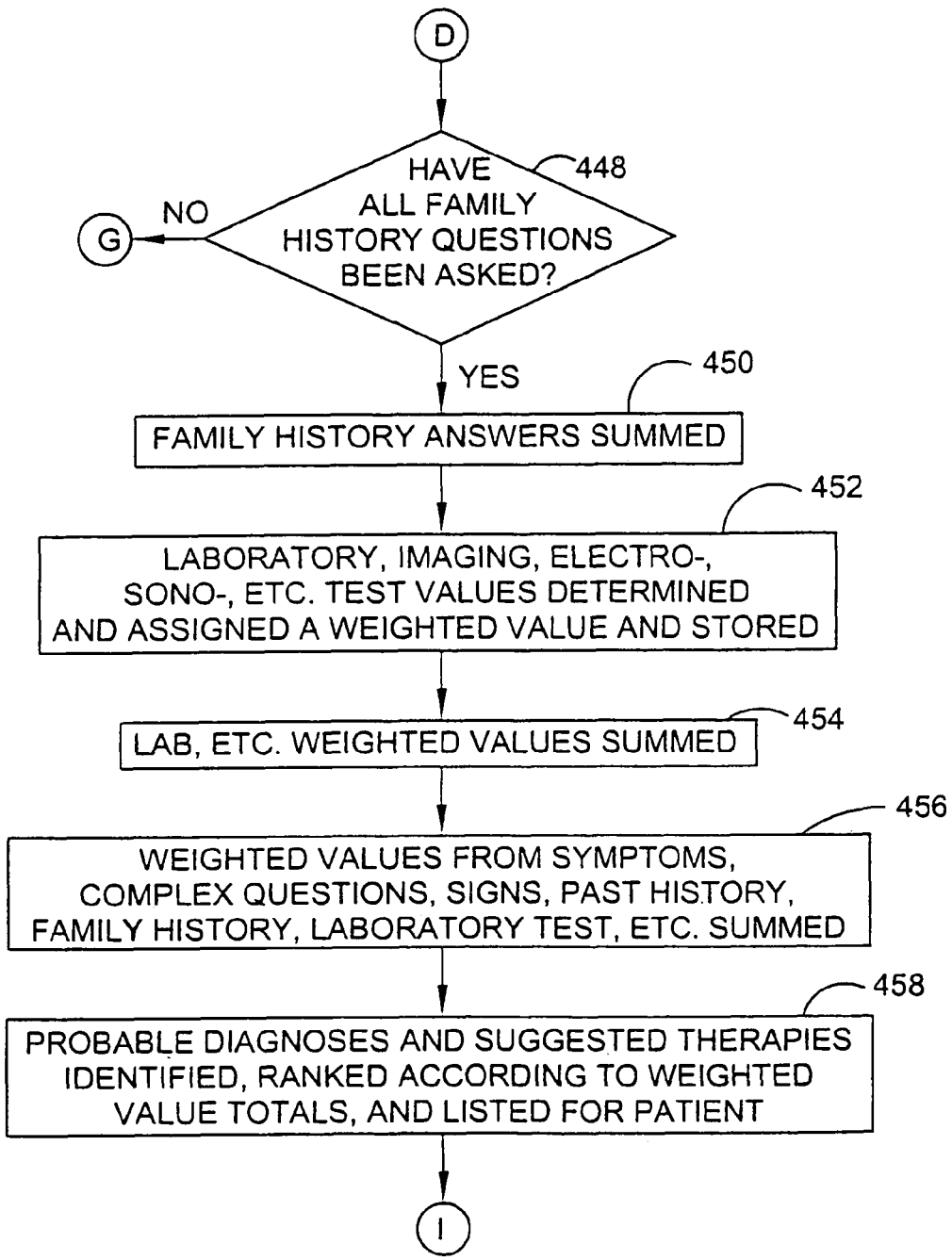
Figure 4E:
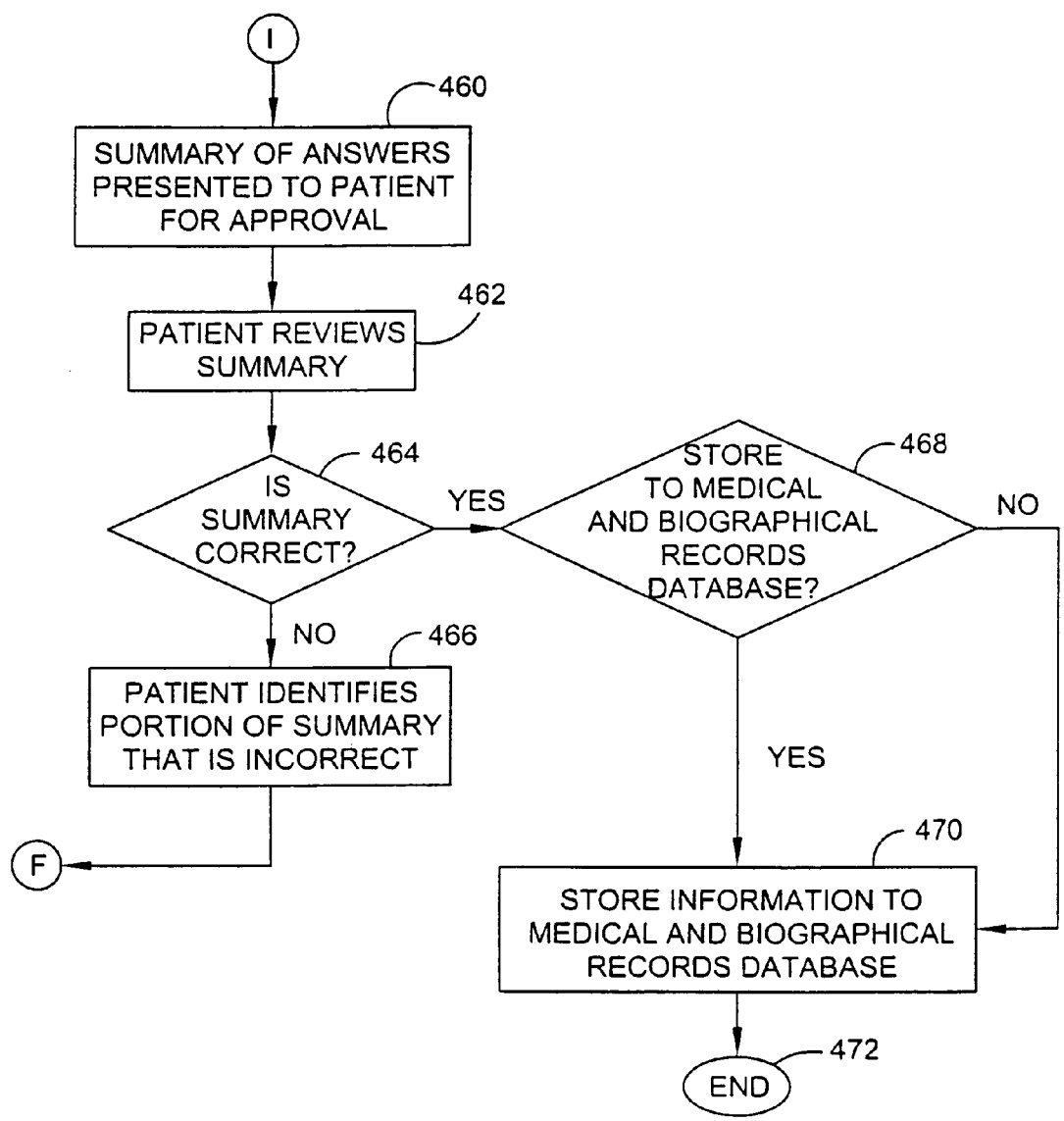

FIGS. 2A-2C illustrate a security process and system used to ensure only authorized individuals gain access to data stored in medical and biographical records 112. Data elements of the system hardware of the present invention are physically separated to prevent unauthorized individuals from breaking into system 100 and gaining meaningful medical and biographical data. Additionally, software filters, designated as "F" in FIG. 2, are present between the elements of system 100 to exclude any extraneous or corrupting files, electronic cookies, or misinformation.

Beginning on FIG. 2A at step 202, an individual connects to central computer 102 via remote computer 108 connected to global network 104. Central computer 102 executes a login routine to ask the individual login questions at step 204 to verify the individual owns one of the medical and biographical records 112 or has been authorized by the owner of one of the medical and biographical records 112 to access the record. At step 206, the individual enters the login information. Central computer 102, at step 208, compares the information the individual entered with stored information of the medical and biographical record owner. If the information entered by the individual does not match the stored information of the medical and biographical record owner, central computer 102 stores information such as the computer address of the individual attempting to login, time, and any information input regarding the login attempt at step 210. The individual is then disconnected from central computer 102 at step 212.

If the information entered by the individual matches the stored information of the medical and biographical record owner, a patient number is obtained at step 214 which corresponds to an individual medical and biographical record 112. The process proceeds to FIG. 2B at step 216 wherein the medical and biographical record 112 corresponding to the patient number is referenced from record database 106. At step 218, central computer 102 determines whether the individual wants to run the medical diagnostic program illustrated in detail in FIG. 4. If the individual does not wish to execute the medical diagnostic program, the process proceeds to step 220 where the patient is permitted to review and add information to the medical and biographical record 112 according to the level of the individual's authority. The process is then discontinued at step 222 and the individual is logged off central computer 102.

If, at step 218, central computer 102 determines that the individual wants to run the medical diagnostic program, the process proceeds to step 224 where a symptom or series of symptoms are presented by the individual. Also, a diagnostic server provides the individual with diagnostic questions attempting to clarify the cause of the symptoms (see medical diagnostic program 116). The individual enters answers to the diagnostic questions via remote computer 108 at step 226. Preferably, a separate answer server stores the answers. At step 228, central computer 102 determines whether any additional diagnostic questions must be asked. If additional questions must be asked, the process proceeds to step 224. If no additional questions need be asked, the process proceeds to step 230 where a summary of answers as identified in FIG. 4E, step 460 are presented to the patient by a separate temporary answer server to verify whether the answers to the diagnostic questions are correct.

Central computer 102 determines at step 232 whether the answers to the diagnostic questions are correct. If the answers are not correct, at step 234 which corresponds to FIG. 4E step 466, the diagnostic program 116 asks the patient to identify the portion of the summary that is incorrect. The process then proceeds to step 224 where the patient is presented with questions by the diagnostic server which correspond to the portion of the summary the patient identified as being erroneous.

If, at step 232, central computer 102 determines the answers to the diagnostic questions are correct, a list of potential diagnoses, preferably listed in the order of most likely to least likely, is presented at step 235. The process proceeds to step 236, which corresponds to FIG. 4E step 468, where central computer 102 determines whether the individual wants to store the diagnostic information in a medical and biographical record 112. If the individual does not want the information stored in a medical and biographical record 112, the process continues at step 220 where the patient is permitted to review and add information to the medical and biographical record 112 according to the level of the individual's authority. The process is then discontinued at step 222 and the individual is logged off central computer 102.

If the individual wants the information stored, central computer 102 stores the information in a medical and biographical record 112 at step 238 then proceeds to step 220.

Health care providers may be charged for the service of transferring patients' recorded medical histories to its own records thereby generating service and access fees. A reliable medicolegal document can be obtained by the health care provider in case of challenges to the amount or quality of the information offered for evaluation.

Remote computer terminals can be located in the offices of health care providers for the individual medical history generation prior to physical examination, interview or therapy. This allows the individual to update information periodically on a timely basis.

In addition to registration, an important component of system 100 involves access. Using variables of the registration information, different levels of access and security can be offered. Access to folio identification requires a minimum amount of identifying data. For example, the input of a patient's full name, without abbreviations, birth date (dd/mm/yyyy), and social security number (SSN) may be used to gain access to general information in the folio. Adding the state or country of birth, plus a health care provider's access number (i.e., BNDD (Bureau of Narcotics and Dangerous Drugs)+ State license number, etc.), for example, allows an internist to access to past history sections of the folio, whereas a pharmacist's access number may allow access to only the medications and allergies section of the folio.

Information regarding use of identification information by an individual accessing a folio may be stored to the folio, thereby leaving a traceable and registered chronological history of the folio being accessed. Making access information available to patients, on demand or during periodic notifications instead of a periodic notification, permits patients to verify whether their folio has been accessed and who accessed it. The access information therefore assures patients that access to their folios is limited to themselves and individuals who they have authorized and that the confidentiality of their folios has been maintained.

For alterations, additions, or deletions to the medical history, the use of a PIN or biometric identification is required for authorization. Otherwise, the entry is considered an unconfirmed alteration, addition, or deletion. Only after a patient's identity or authorization is confirmed would the entry be considered official. Entries may be color-coded to distinguish unconfirmed information in a folio. The same method of verifying official entries may be followed for entries of medications, lab results, etc. Therefore, official data is incorporated in the folio as such only with approval of the authorized individual or patient, unapproved data is labeled or color-coded as such.

In addition to the verification methods described above, patients may be issued a magnetic strip card, similar to a credit card, on which all of the identifying information may be stored. The patient's PIN or biometrics identification should not be stored on the magnetic strip card. Rather, this identifier is preferably supplied separately before access to a patient's folio is granted. The folio is divided into separate sections of medical and biographical information permitting sensitive information maintained in the folio to be protected in controlled access areas. Controlled access areas require reentry of the PIN, entry of a different PIN, or biometric information to permit viewing. Entry of an additional, different PIN is required to permit information to be copied or transferred. Requiring additional levels of identification of access authority is designed to increase security, and to prevent unauthorized disclosure of patient medical and biographical information, as well as to increase patient confidence about folio confidentiality.

In emergency situations, when patient authorization via PIN or biometric information is not available to enable emergency health care professionals to gain access to a patient's folio, an emergency summary package, containing vital information only, is made available to a properly identified emergency institution. Thus, the confidentiality of a patient's folio can be protected, even in emergency situations, by ascertaining folio access authorization, keeping records of these releases, and properly informing the patient when emergency releases are made. Furthermore, the present invention provides superior benefits over existing medical record systems as emergency personnel may be able to obtain vital information, regardless of whether the patient is at home or in another state, in the event the patient is incapacitated. This permits emergency health care professionals to treat the patient more rapidly and with more confidence than they could without obtaining the patient's vital information.

In addition to centralized, medical, and biographical records database 106, the present invention also includes medical diagnostic program 116. The medical diagnostic program 116 is preferably a confidential, personal, and continuously available electronic consultant that is available to individuals who have access to a computer with access to computer network 104. Similar to the medical and biographical record database 106, the medical diagnostic program 116 would reside on central computer 102 connected to network 104. While individual registration for a medical and biographical record 112 is not required, information can be stored to a registered patient's folio if the patient requests the recording.

FIG. 3 identifies an illustrative set of answer weighting values and corresponding frequency categories which correspond to expected frequencies of the answers to diagnostic questions for a given disease. Two frequency categories are identified. The first category of identified frequencies is more preferred as it permits more narrow frequency delineations while the second category of identified frequencies provides less exact delineations to be made for a given answer. The answer weighting in the preferred categorization ranges from −10 to 10 based on a frequency range of "impossible to be connected to diagnosis" to "indispensable." The answer weighting in the second frequency categorization ranges from −9 to 9 based on a frequency range of "Very strong indication for different diagnosis" to "Very strong."

The assigned weighting value for an answer may be different for different diseases based upon the frequency the answer is expected. In the example of FIG. 3, the answer weighting value of "10" may be assigned for the diseases of angina, myocardial infarction, and pulmonary embolus if "yes" is answered for the diagnostic question, "Are you experiencing chest pain?" as the symptom is indispensable to all three diseases. Conversely, an answer weighting value of "5" may be assigned to the disease of pneumonia since the frequency of the symptom is common to the disease, but not necessarily indispensable in patients with pneumonia.

An answer weighting value can also detract from the likelihood of a particular disease being diagnosed if the frequency of the answer ranges from unlikely to occur to impossible to be connected to a given disease. Such negative weighting indicates that the answer to the diagnostic question may suggest the diagnosis of a different disease. For example, the answer weighting value of "0" may be assigned for the diseases of angina, myocardial infarction, and pulmonary embolus if a patient responds "no" to the question, "Are you experiencing back pain?," as the symptom is rare or unusual for those diseases. Conversely, an answer weighting value of "−3" may be assigned to the disease of carotid artery dissection since the frequency of the symptom is "very unlikely to occur with diagnosis," or the answer is a "potential indication for a different diagnosis."

The assigned values, value ranges, and frequency categories may be modified to enlarge or reduce the values or frequency categories without being outside the scope of the present invention.

FIGS. 4A-4E illustrate an exemplary overview flowchart of the medical diagnostic program process. The process begins with step 402 in which a patient inputs symptom(s) being experienced. Also at step 402, medical diagnostic program 116 asks a diagnostic question about the health symptoms being experienced by the patient. At step 404 the patient answers the question by inputting either "yes" or "no" as the only possible responses to the question. An answer must be received from the patient in order for the process to continue. A weighted value is assigned to all potential diseases at step 406 according to the patient's response to the diagnostic question. The weighted values for all the potential diseases are stored to memory. Next, at step 408, the process determines whether the patient has been asked and has answered all required health symptoms questions. If all required health symptom questions have not been asked, the process loops back to step 402 and asks the patient another health symptom question. If the patient has been asked and has answered all health symptom questions, the weighted values for each potential disease are summed in step 410 to produce a total weighted value for health symptoms for each potential disease. The total weighted value for each disease is stored to memory.

The process continues at step 412 where the patient is asked a complex symptom question. Complex symptom questions include "and, or, not, both, or none" type questions and combine a plurality of symptoms in each question. At step 414 the patient answers the question by inputting either "yes" or "no" as the only possible responses to the question. An answer must be received from the patient in order for the process to continue. A weighted value is assigned to all potential diseases at step 416 according to the patient's response to the diagnostic question. The weighted values are then multiplied by a pre-defined value determined according to the importance of the answer to the complex question for a particular disease. The weighted values for all the potential diseases are stored to memory. Next, at step 418, the process determines whether the patient has been asked and has answered all complex questions. If all complex questions have not been asked, the process loops back to step 412 and the patient is asked another complex question. If the patient has been asked and has answered all complex questions, the weighted values for each potential disease are summed in step 420 to produce a total weighted value for answers to complex questions for each potential disease. The total weighted value for each disease is stored to memory.

The process continues from step 422 through step 450 for questions relating to health signs, patient past history, and family history and other types of medical, health, or biographical information in the same manner as described above. When medical diagnostic program 116 is used in conjunction with medical records database 106, this information may be automatically retrieved from the patient's individual record 112.

The process continues at step 452 where laboratory, imaging, electro-diagnostic, sonographic, and other test results stored in patient medical and biographical records 112 are determined and assigned a weighted value based upon the frequency of the test results occurring for a given disease. The weighted values assigned to the potential diseases are stored to memory. At step 454 the weighted values assigned for the test results for all the potential diseases are summed to produce a total weighted value for test results. The total weighted value for test results is then stored to memory. Next, at step 456, the process sums the total weighted values for health symptoms, complex questions, health signs, patient past history, family history, and test results to produce an overall weighted value for each disease. The diseases are preferably ranked by probability of being correct from the highest to the lowest score.

At step 458, diseases and suggested therapies to treat the diseases are listed to the patient as probable diagnoses and treatments according to the overall weighted values for the diseases. The probability that the patient actually has a listed disease increases correspondingly to the overall weighted value for a disease. Thus, the disease with the greatest overall weighted value is the most probable diagnosis for the patient, and the disease with the smallest overall weighted value is the least probable diagnosis. At step 460, a summary of the answers to the diagnostic questions is presented to the patient for review and approval.

At step 462, the patient reviews the summary of the answers. At step 464, the patient is asked whether the summary correctly states what the patient had meant to input. If the patent indicates that the summary is incorrect, at step 466 the patient identifies the portion of the summary which is erroneous. The process then continues at either step 402, 412, 422, 432, or 442 and the patient is presented with questions corresponding to the portion of the summary which the patient identifies as being erroneous. Upon answering all the questions, the answer values are summed in either step 410, 420, 430, 440, or 450 and the process continues to any other portion corresponding to a portion of summary which the patient also identified as erroneous. If no other portion was determined to be erroneous, the process continues at step 456.

If, at step 464, the patient indicates the summary is correct, the patient is asked at step 468 whether the diagnostic information should be stored to a medical and biographical record 112 belonging to the patient. If the patient responds affirmatively, the diagnostic information is stored to the patient's medical and biographical record 112 at step 470 and the process is ended at step 472. If the patient indicates that the diagnostic information should not be stored in the patient's medical and biographical record 112, no storage to is conducted and the process is ended at step 472.

FIG. 5 illustrates, in tabular form, a correlation between diagnostic questions, diagnostic codes, patient responses to diagnostic questions, and the value weighting assigned to different diseases for responses to the diagnostic questions. For identification purposes, individual cells are identified by column number and row number (column, row). FIG. 5 is merely one example of how diagnostic information may be processed and is not meant to be limiting as to the broad scope of manipulating the medical diagnostic information of the present invention.

Column 502 lists the various categories and subcategories of questions asked the patient. Column 504 lists the unique code identifier for each question presented to a patient. Column 506 lists the patient's responses corresponding to the questions listed in column 502. If the patient responds "yes" to a question listed in column 502, a "111" is stored in column 506. If the patient instead responds "no" to the question, a "000" is stored in column 506. For purpose of processing the questions and answers, the answer code "111" or "000" is appended to the code for the question. Once the patient inputs an answer to a diagnostic question, an answer weighting value is determined for the answer which corresponds to the diseases listed in columns 506, 508, 510, 514, and 516. For example, a patient is asked a health symptoms question relating to whether the patient is experiencing chest pain (502, 518). The code for chest pain is identified as 0000030001 (504, 518). The patient responds "yes" to the question, indicating that the patient has experienced chest pain. Upon receiving a "yes" answer, "111" is stored in answer cell (506, 518). The diseases of angina, myocardial infarction, and pulmonary embolus each have an answer weighting value of 10 for a "yes" response as the symptom, according to FIG. 3, is indispensable for those diseases. An answer weighting value of 10 is then stored in cells (508, 518), (510, 518), and (512, 518) respectively. As the symptom of chest pain for aortic artery dissection is very important, but not necessarily indispensable according to FIG. 3, a value of 8 is stored in the aortic dissection cell (514, 518), corresponding to the symptom of chest pain. For the disease of pneumonia, the symptom of chest pain is common according to FIG. 3, and therefore a value of 5 is stored in the pneumonia cell (516, 518).

Similarly, the patient is asked whether he or she is experiencing abdomen pain. The patient answers "no" to the question, indicating that abdomen pain has not been experienced. Upon receiving a "no" answer, "000" is stored in answer cell (506, 520). The diseases of angina, myocardial infarction, pulmonary embolus, aortic dissection, and pneumonia each have an answer weighting value of 0 for a "no" answer as the symptom, according to FIG. 3, is either rare or is irrelevant to determining a diagnosis for those diseases. An answer weighting value of 0 is then stored in cells (508, 520), (510, 520), (512, 520), (514, 520), and (516, 520) respectively.

Next, the patient is asked whether he or she is experiencing back pain. The patient responds "no" to the question, indicating that back pain has not been experienced. Upon receiving a "no" answer, "000" is stored in answer cell (506, 522). The diseases of angina, myocardial infarction, pulmonary embolus, and pneumonia each have an answer weighting value of 0 for a "no" answer as the symptom, according to FIG. 3, is either rare or is irrelevant to determining a diagnosis for those diseases. An answer weighting value of 0 is then stored in cells (508, 522), (510, 522), (512, 522), and (516, 522), respectively. Back pain, however, is very unlikely to occur with carotid artery dissection and therefore, according to FIG. 3, an answer weighting of −3 is stored in cell (514, 522).

This process continues until the patient has been asked and has answered all diagnostic questions selected by the diagnostic program 116. The answer weighting values are then summed for each disease column to produce an overall weighting value for each disease. When all the answer weighting values are added together, the negative values assigned to answers unlikely to be given for a given disease lower the overall weighting value of a disease while the positive numbers increase the overall weighting value of a disease. The overall weighting value for angina is 256 which is stored in cell (508, 524); the overall weighting value for myocardial infarction is 285 which is stored in cell (510, 524); the overall weighting value for pulmonary embolus is 170 which is stored in cell (512, 524); the overall weighting value for aortic dissection is 111 which is stored in cell (514, 524); and the overall weighting value for pneumonia is 27 which is stored in cell (516, 524). Thus, given the abbreviated example listed in FIG. 5, the patient would receive a list of potential diagnoses, in order of most likely to least likely, of myocardial infarction, angina, pulmonary embolus, aortic dissection, and pneumonia.

According to a preferred embodiment of the invention, data may be acquired by directed data acquisition and/or interactive interview or inquiry. Directed data acquisition represents all data acquired by the medical diagnostic program from direct entry of information, and not by interactive interview. Examples include vaccinations, birth and developmental data, previous diagnoses and prescriptions, present and past medications and therapies, surgeries and findings, pregnancies and deliveries, review of systems, habitual and social history, family history, and so forth. This information is individually supplied data which is not generated by the diagnostic questions, such as data present in a patient's folio, or supplied by a third party and approved for entry into a patient's folio after review and approval by the patient.

In another embodiment, the diagnostic program may also be used by a health care professional in the same manner as it is utilized by a patient. Information may be input while a patient is being interviewed, as well as from medical records and notes taken by a health care professional during an examination. The potential diagnoses list may then be displayed to the health care professional and also be approved by the health care professional for entry into the health care provider's medical and biographical record for the patient.

Program 116 obtains information from an individual through an interactive interview. The interactive interview consists of multiple-looped pathways that direct the medical diagnostic program to present appropriate diagnostic questions to the individual and simultaneously weight the answers. The distinguishing characteristic of this system is that data is obtained by sequential questioning that can only be answered in the affirmative (yes) or the negative (no). Entry of single or multiple symptoms, signs, conditions, diagnosis, medications, or treatments, initiates the interaction.

Laboratory, radiology, or pathology information is integrated as available through the directed data acquisition as described above.

Starting from simpler to more complex pathways, different levels of sophistication are addressed and satisfied. The interview is constructed in a clinical format, exhaustively asking the individual diagnostic questions in the how, when, what, where, and why format in order to reach potential diagnosis. Graphics, in the form of diagrams, models, pictures and illustrations (body, system, function, and so forth) are part of the inquiry, requiring individual interaction to help pinpoint areas where symptoms are being experienced. Degrees of intensity, frequency, duration, and so forth are digitized and/or color-coded for estimation of severity. Sidebar illustration or diagrams are used to clarify questions or guide responses. Hyperlinks are made available to the individual to assist the individual to define, clarify, amplify terms, conditions, diagnosis, recommended therapies, etc. Examples of hyperlink languages that can be provided include 1) conversational or general public; 2) scientific oriented; and 3) medical terminology.

In one embodiment, three-dimensional and holographic imagining illustrating questions and answers are used to further refine the information. No diagnosis is considered or reached until all the symptoms and signs have been elicited and examined. From the list of potential diagnoses, further questions may be raised to refine the probability sequence. This method or particular approach mimics the ideal that no diagnostic assumptions are made until all the information is elicited. Thus, the method of the present invention avoids the introduction of any bias which may result in the correct diagnosis being missed.

As many complaints and modifying adjectives as can be collected are utilized to cross-match with the presenting complaints. Each complaint is examined individually to ensure the meaning of each complaint is correctly understood. Different combinations of symptoms are examined to define their relationship to the health condition being experienced by the individual. These are also examined in the Y/N format. A number of questions, including instructions to elicit signs, would be provided to the individual to answer.

With sufficiently detailed elicited information, and without the benefit of a physical exam, it is highly probable a reasonable and correct diagnosis may be obtained. Additional information on health related signs may be obtained by directing the individual to perform easily described tasks and to record the results. When technology permits, electronic examinations via electronic audiovisual sensors can be used to further corroborate or expand the information basis. Such information can be obtained from electronic audiovisual sensors connected to remote computers collecting patient anatomical data, biochemical data, physiological data, and pathological data hereinafter collectively referred to as health data. Examples of health data include, but are not limited to, body temperature, metabolic profiles, organ function tests, laboratory data, radiological and imaging data, dermatological data, otologic and ophthalmologic data, nervous system data, cardiovascular data and so forth. An example of audiovisual sensor information collection is the collection of cardiovascular, sounds via phone-modem. The individual is then reexamined in the yes/no (Y/N) format to further corroborate the data obtained from the audiovisual sensors.

A series of strategies can be designed to instruct and guide the interviewee into eliciting pertinent positive or negative signs to further refine the diagnoses. With the rapid progress of providing and obtaining audiovisual information on the Internet, obtaining an extensive exam via audiovisual information may also be used to further the diagnoses. An example would be cardiopulmonary, abdominal, and peripheral vascular auscultation. With sophisticated programs, many of the obtainable cardiac, vascular, pulmonary and abdominal sounds and rhythms, combined with a careful history interview can be very sensitive and precise in identifying potential diagnoses. Static or continuous visual digital images transmitted via Internet would nearly obviate the need for most personal encounters between health care provider and patient. Hyperlinks could be readily available to guide the examination by giving detailed step-by-step instructions.

By using the present invention, an individual can prepare for a medical appointment or examination. By executing the medical diagnostic program, an individual is presented with potential questions that would likely be asked during an actual medical appointment or examination. Thus, the medical diagnostic program prompts the individual to recall and verify potential patient history or medical information that may be important to provide a health care professional during the individual's actual medical appointment or examination.

Potential diagnoses are offered in list form identifying potential diagnoses from most too least likely condition. Recommendations, including further inquiries, tests, therapeutic methods, or consultants are posted for the individual to review. Local, regional, and national health care provider listings are also posted with further pathways for deeper exploration of credentials, etc.

Drug reference sources, i.e., PDR, toxicology, and so forth, are part of the immediately available information. In addition, correlation of treatment and side effects can be rapidly interconnected. Adding commentary by experts on recent advances in diagnosis or therapies, including experimental work (using pro and con sides) further enhance the usefulness of the diagnostic program.

Although computer presented information is typically visually based, the present invention may be transformed to an audio format that further extends the reach of the method for dyslexic, blind, or illiterate persons.

The interactive multi-looped interview will require the input of many specialists. To attain efficiency, practicality and balance, each section will benefit from input from academic and non-academic health care providers. Physicians, nurses, therapist, counselors, clergy, etc. are considered specialists in their areas or sections.

A further embodiment of the present invention can be applied to insurance processing as a source of insurance services and revenue. Data contained in the medical records database, as well as information generated from the medical diagnostic program, can be integrated to provide insurance review systems necessary information to review, approve, and/or pay for health care transactions. Examples of insurance company services that are particularly suited to use information stored in the medical and biographical database consist of terms of insurance contracts, explanation of benefits and services, pre-approval of patient services, pre-approval of treatment, approval of treatment, verification of eligibility for medical treatment, verification of treatment, and automated payment of medical treatment by insurance companies. Thus, an insurance review system can be implemented using the structure of the present invention that would satisfy the most demanding of all reviews, at a reasonable cost and expediency, while at the same time preserving privacy and confidentiality.

Treatment and testing redundancy occurs frequently in the present medical care environment due to the absence of a common repository of information and its ready availability. An immediate benefit to insurance providers utilizing the present invention would be the elimination of unnecessary tests, procedures, operations or treatments that have already been done, prescribed or tried, thereby reducing redundancy and repetition of failed therapies. In addition, tests, procedures, treatments, or operations that do not satisfy previously established criteria threshold could be halted immediately. Conversely, if a health care professional strongly feels that the recommended test, procedure, treatment or operation is necessary, immediate feedback would allow him or her to satisfy the criteria or else present the necessary argument to a reviewer to obtain permission to proceed. The reviewer would have all the necessary information immediately available to approve or refuse the request. All of these functions could be performed with full preservation of confidentiality.

Insurance provider screening criteria can contain patient medical information, contract parameters and stipulations, allowances, restrictions, requirements, and characteristics of the insurance plan or coverage in which an individual is a participant. An insurance provider can immediately know whether a prescribed service, treatment or medication is covered by the particular plan and to what extent. Because updates to the criteria can be implemented immediately, the frequency of errors and non-covered procedures could be substantially reduced, resulting in significant savings for all involved.

One of the elements of checks and balances in the insurance review system is patient review of the entered data. Since the records belong to the patient, if a patient disclaims the veracity of the data upon reviewing entered data, an immediate denial of an insurance claim and subsequent investigation would be triggered. Any health care professional with multiple denial events could lose the privilege to participate in the program.

Even with the above checks, a patient and a health care professional could agree to abuse the system. Single or multiple violations may escape detection; patterns of abuse may eventually become evident, however, by comparing deviations from patterns of other health care professionals. Substantial deviations can automatically be culled out, permitting close scrutiny of activity and much earlier detection of fraud than occurs in current insurance practices. One potential remedy, for example, can be requiring a second opinion or review by an independent consultant selected by the third party payor or the obtaining of laboratory studies to confirm a disorder or the intake of medications, and so forth. Due to the explosive growth of medications, alternative brands, and generics, there is a real risk that even the best informed and intentioned of health care professionals may miss an unintended interaction or secondary effect of a medication added to other medications already in use or to an underlying condition. By integrating all available information for a given patient and referring to massively stored drug information, undesired events could be significantly reduced, albeit not eliminated completely, due to the inability to infallibly predict all the potential reactions of one particular individual to a given biochemical combination. In spite of being able to completely avoid undesired events, the potential savings in terms of reduction of iatrogenic injury, wasted medications or therapies, and prevention of costly side effects are great.

Another potential application is allowing insurance provider reviews to be conducted remotely while still protecting privacy and confidentiality of the patient and the medical and biographical data. The requesting reviewer can submit the necessary identifying data and permission from a patient to obtain medical and biographical data. The identification server would select the secret random number assigned to that specific patient, select the required information and delete identifying data (i.e., names, nicknames, initials, birthdays, addresses, etc.) and submit anonymous records to the reviewer. Of course, a single patient request would be difficult to disguise, but the assumption is made that multiple charts would be requested by any one reviewer, diminishing significantly the chance of individual identification. Because of this potential breach of confidential information safeguarding, the first alternative is more secure and the preferred one.

The utilization of the present invention by insurance providers would substantially reduce the cost of service, review, delays and while maintaining confidentiality of patient medical and biographical data. By acting as a neutral intermediary, and at the same time facilitating services for the user and cost controls for the payor, a fee for utilizing the services of the present invention should be cost effective for insurance providers.

In one aspect of the insurance processing embodiment, an insurance provider is given access to review a patient's medical and biographical record. The insurance provider's contractual criteria for coverage is compared to the medical treatment claimed and the patient's medical and biographical record which contains medical tests, diagnoses, treatments, and so forth. If the medical treatment prescribed is contractually covered by the patient's insurance policy, payment is made for the treatment. If the treatment is not within the covered policy, however, a rejection to the claim is made. As the present system maintains data in digital codes, the comparison of the treatment to the patient's medical and biographical record which contains medical tests, diagnoses, treatments, and so forth may be performed either by an individual or by automated means.

Automated comparison of treatment to a patient's medical and biographical record provides additional confidentiality to a patient's medical and biographical data as a computer could simply compare diagnoses and treatment codes to the codes covered by the insurance provider. This method results in a qualitative approval or rejection of a claim being output by the computer rather than an individual looking at a patient's medical and biographical data the patient desires to remain private.

In yet a further aspect of the insurance provider embodiment, a third party intermediary obtains the insurance provider's digital codes for medical treatment that the insurance provider covers in its policies and compares them to the medical treatment digital codes to the digital codes contained in the patient's medical and biographical record. If the insurance provider's policy criteria (e.g., terms of insurance contracts, explanation of benefits and services, etc.) are satisfied for a medical treatment, the third party informs the insurance provider that it should pay for the medical treatment claim. If the criteria is not met, the third party informs the insurance provider to deny the medical treatment claim. This comparison and subsequent instruction to pay or deny a claim may also be made by an individual employed by the third party or via automated means. Thus, by using a third party, a patient's medical and biographical data are kept confidential from the insurance provider.

Yet a further embodiment of the present invention is the use of the centralized medical and biographical records system as a database from which medical insurers may determine health care costs and determine insurance premiums in a cost-effective manner.

Another embodiment of the present invention is a health care financing and insurance system. Areas of difficulty in the present health care system are the verification of health care services rendered and reasonable financing of the services. A successful system should be equitable and balance the needs of the insured patient (satisfaction of medical, emotional, sociologic and psychological needs and desires), the health care providers (physicians, hospitals, etc.), the employer, and the insurance industry.

The characteristics necessary for a viable and functional system include: (1) Simplicity—to make it easily understandable, applicable and enforceable; (2) Affordability—so that the majority of the population could benefit; (3) Equitability—so that financial input results in clear and tangible benefits to all; (4) Confidentiality—to ensure the necessary information is correct and safe; (5) Financially attractive—to encourage participation; (6) Rewarding of behavior that benefits one's health; and (7) Monitoring and outcome evaluation to continually improve care.

Cooperation of parties such as the patient, the employer and the government is needed for such a system to succeed. Needed information includes a complete, up-to-date patient history, a comprehensive examination, full integration of family and genetic history, patient education as to therapies (preventive, conservative, medical, surgical, and working differential diagnostic plan), and therapy effectiveness and cost. Also necessary would be the implementation of effective monitoring, corrective procedures, and outcome evaluation.

The system of the present invention can balance all of the above requirements and provide the necessary basis for development of an improved health care finance and insurance system. By compiling all the available and necessary medical information and recommendations, such as the specific diagnosis and prescribed services or treatments, rapid verification of appropriate diagnostic or therapeutic decisions can be made according to criteria for approved therapeutic methods for specific diagnoses. If a health care provider disagrees with a denial of services, it can quickly input corrective information to satisfy the requirements. Since patient verification of facts is required for final approval, the amount of false information or misrepresentation can be substantially reduced, albeit not eliminated. Dishonest practitioners could still manipulate the system; however, unusual or abnormal patterns of behavior could be eventually sifted out and those practitioners monitored closely or eliminated from the roster of approved providers after appropriate application of protocols.

The most effective way to control costs is to share financial burden with the patient. By providing education and information, decision-making empowerment is conferred to the patient. By imposing a portion of the expenses on the patient, reluctance to ignore fiduciary responsibility is reduced significantly. Adding financial incentives and rewards may beneficially engender a high degree of patient cooperation.

Employer cooperation entails full and honest disclosure of financial package awarded to each individual in the program. Levels of financial reward, rather than exact amounts may suffice.

Verification of income level of individuals would require governmental cooperation.

In several embodiments of the health care finance and insurance system of the present invention, rights are dependent on the level of financial burden. The most equitable formulation ties the financial burden to level of income and wealth. Some possible embodiments include:

1) Insurance premiums bracketed to income level: An insurance premium for standard coverage at no more than 5% of gross income, plus an out-of-pocket cap of another 5%, with maximum financial exposure set at a certain top level of income. This structure could limit the total care expenditure to no more than 10% of gross annual income for most individuals or families with lesser percentages for those whose income exceeded the top limit. Inequities may still exist in this embodiment as one family may spend less than 1% of gross income per year, another may spend close to 5% of gross, another may spend 50% of gross, pay only 10%, and use up the pooled contributions of others.

2) Tiered coverage: Universal coverage for all, limited to 1% of gross individual annual income. Scaled added coverage of progressive premiums with two or more levels add alternatives or layers of comfort or coverage to a basic health plan.

3) Self-insured package: Targeted to large companies or conglomerates of smaller companies. For example, companies may contribute a fee representing 60% of the estimated premium while the employee contributes 40%. The pooled contributions then pay the approved expenses covering 60% and the patient paying the other 40% out-of-pocket. Out-of-pocket expenses are limited to a set level of income. Coverage above the set level is at 100% of approved expenses.

Because a 40% co-payment by the employee is required, the employee, in conjunction with the present invention, acts as a gatekeeper and overseer of the account. The present invention can find the extremes and the average costs of health care provider activities and inform the user of the reasonable costs of services. The user can then negotiate a reasonable fee for services based on the information or pay a higher cost from out of pocket if the user so desires. The insurance coverage of 60% would remain based on average or standardized fees; thereby limiting the pay-out. The above percentages may be varied in the self-insured package to meet the varied needs and financial capabilities of both the employee and employer.

A health care finance and insurance method can be structured on the biological and medical database of the present invention that can compare patient records approved treatment methods, approve or disapprove payment, and also act as the insurance management system which collects premiums and contribution monies, and pays for approved services or treatments. The health care finance and insurance method therefore must have access to health care, financial, and insurance policy information. Additionally, if the system is also to pay for the medical expenses, it must receive premiums and co-payments and have access to financial accounts.

Thus, a health care finance and insurance method based on the present invention would maintain medical, biographical, diagnostic, and treatment records for a plurality of individual patients in a medical and biographical records database on a centralized computer. Insurance service and policy information would also be maintained. Examples of the service information include terms of insurance contracts, explanation of benefits and services, pre-approval of patient services, pre-approval of treatment, approval of treatment, verification of eligibility for medical treatment, verification of treatment, and automated payment of medical treatment. Relevant policy information includes the approved treatment methods for diagnoses. This enables the system to compare patient diagnosis and prescribed services or treatment records present in the medical and biographical records database with the approved therapeutic treatment for the identified diagnosis. From this information, the system would either approve or disapprove payment for the prescribed services or treatment.

Regarding the financial aspects of the system, health care coverage information maintained for individual patients would identify the patient and insurer contributions to a health care policy. The insurer may be a typical insurance company, an employer, or other insuring organization. The system would also maintain financial accounts to hold health care premiums and payments of health care treatments received from the patient and the insurer or employer. From these accounts, the system would pay the health care provider for approved treatments. The patient would then bill the patient for their co-payment contribution proportions identified in the insurance policy.

A self-insured package based on the present invention would be beneficial to companies by significantly trimming costs by eliminating repetitious, erroneous, or unnecessary testing or treatments. The health care financing and insurance system embodiment of the present invention would act as a manager or managing system by discriminating between adequate and non-adequate therapies. On the other hand, the individual is still free to pursue whatever avenues of treatment or investigation he or she desires, as long as the individual is willing to carry the financial burden. Eliminating middle managers and clerks would substantially add to the savings and give incentive to the companies to promote this particular form of health care.

Economics, degree of health services, security and confidentiality of records, accessibility, and availability provide incentives to the individual to participate in the new, developing form of health care utilizing the present invention. By using electronic communications and multiple interactive formats, accessibility and availability can be readily solved. Security and confidentiality of records require utilizing technology that provides a high degree of security after relatively minimal education on its use.

Degree of health services is where a great deal of sophistication and development is necessary to provide all the necessary and desired services; the goal should be directed towards preventive medicine rather than on therapeutics. If a solid system of preventive medicine can be developed, the cost of health care can be reduced substantially.

Economics is perhaps the most difficult and perhaps also the biggest incentive to participate in this system. The financial incentive has to be sufficiently obvious and desirable to most individuals to obtain their cooperation. Structuring the incentives will determine the level of success of the system.

The sponsoring companies should have reasonable financial and human resource benefits to entice them to offer the services. At the present and foreseeable rate, health care expenses represent an enormous drain on any company. The drain comes in two main fashions: direct cost and payments, and indirect costs due to lost or impaired productivity and damages. Worst of all, the present system of care is devoid of the necessary incentives to stimulate the individual to actively engage in preventive rather than therapeutic care. Creating a formula that encourages individuals towards prevention is not an easy task, as numerous failures have occurred in the past. Reducing direct costs can only be achieved by shifting part of the financial responsibility to the individual; this represents a reversal of the past 40 year trend and a difficult sell job unless substantial benefits to the individual can be added to the equation to sway the balance. By improving the overall health of the work force and reducing unproductive activities, further benefits to the company will accrue.

Data may be entered into database 106 using any conventional means. For instance, data may be entered via a keyboard, touch screen or speech recognition interface. Further, preexisting source documents (i.e., paper originals and the like) may be scanned into database 106 and saved as a document image forming an individual record 112, a plurality of records or a portion of a record. In one embodiment, the scanned documents are stored in a lossless compression format such as Tagged Image File Format (TIFF) on multiple servers. The servers are both physically and electronically secured (i.e., with security software and hardware) to prevent unauthorized access. Once the document is placed in storage, no updates are allowed.

The lossless compression format of the scanned documents prevents forgery of the preexisting records stored in the database because the lossless compression format is always stored and viewed in the same way. Thus, a suspect document can be compared to a stored original or master for authentication. If no changes have been made to the document, the stored original and the copy will be identical on a pixel-by-pixel basis. If changes have been made, the original and the copy will not match.

The scanned document images are available for viewing by appropriately authenticated users. The users must have prior registration or meet other identification criteria as set forth above to prevent access from being provided to unauthorized users. Further, document access is logged so the time, date and location of the user is recorded during each access. Preferably, the scanned document images are accessible using conventional browsers. Because the stored images may be large, other formats (e.g., GIF or JPG format) can be used for viewing. However, it is desirable for at least one original to be stored in a lossless compression format for authentication purposes as explained above. Images of scanned documents can also be transmitted via email, facsimile, or printed and/or delivered via conventional means such as post or courier.

In one embodiment, each document image is watermarked. Both visual and digital watermarks may be used. One example of a visual watermark includes a two-dimensional barcode. The barcode may be imprinted on the scanned document image prior to storage. Alternatively, the barcode may be applied to the image after scanning. Preferably, the barcode includes encrypted information such as ownership, access rights and a checksum for initial authentication purposes. In one particularly preferred embodiment, the two-dimensional barcode includes at least 128 bits of encrypted data imprinted on a blank portion of the document. When document images are copied, e-mailed or imbedded in other documents, the visual watermark may be used to identify the document as coming from database 106. Preferably, every document stored in the system is traceable back to the original. The visual watermark aids in tracing. Any document leaving the system, for example by facsimile or mail, may be traced back to the original. Any documents with an altered or obliterated visual watermark are deemed not original and their authenticity is suspect.

The digital watermark is embedded in the electronic copies of the documents. This watermark, although not viewable by browsers, also is used for tracking and authentication. Each document is marked with machine-readable encrypted data including the source, subject, access level and a unique subject dependent document identifier. Thus, the digital mark allows machines to recognize and index the document regardless of the scan order. Further, the document identifier prevents redundant storage of identical documents if desired. By putting the document identifier inside the data, the stored documents need not adhere to any particular naming convention. Further, it is envisioned that the document identifier will eliminate many organizational problems related to converting paper records to electronic format.

The scanned document may be analyzed via optical character recognition to gather key words and phrases to allow automated indexing of the contents of the document. Such indexing allows searching to quickly find and retrieve documents containing certain words or phrases.

In one embodiment, a computerized system is used to sort and index documents. The system is particularly useful where vast archives of documents have been compiled. It is envisioned that these documents may contain a wide variety of information in various formats and may be handwritten or computer generated. After a record is scanned into the system, an image file is generated for each page of the scanned record. The image files are introduced to a document analysis indexing program. The program analyzes each image to produce a visual key signature which will be described in further detail below. The visual key signature is compared to each of the signatures in a database of known visual key signatures that uniquely identify the document as being of a specific type. If the visual key signature matches a known signature, the image file is paired with a corresponding index analysis template for further processing. If the visual key signature does not match any known signature, the image is reanalyzed with modified criteria to find a signature match. If a signature match cannot be found, the image file is held for human analysis to determine whether a new form is being introduced to the system or whether the form is severely damaged.

Once an index analysis template is found, components of the image are analyzed to determine the content of the image. The type of data corresponding to each component of the image is known for a given index analysis template. Thus, only those areas of the image where data required for indexing are found need be analyzed during the image analysis. Characters and symbols within each component are analyzed using optical character recognition to provide the data necessary to properly index the image. When the analysis is complete, the image files are sorted and indexed by unique and common identifiers obtained from the visual key signature and index analysis template processes.

When documents that already have barcodes or other watermarks are examined using the methods described above, the watermark data is extracted to form an additional indexing element. Documents that do not have barcodes or watermarks will receive a uniquely identifiable watermark that can be used to match the original hardcopies of the document with the original electronic files. Further, it is envisioned that the computerized system for sorting and indexing documents will initially perform a check to determine whether a watermark exists prior to analyzing the image to find a visual key signature. If a watermark is found and the document has already been indexed, the step of analyzing the image for a visual key signature is unnecessary and may be skipped.

The visual key signature is composed of a uniquely identifiable set of visual keys. The visual key signature process applies transformation filters to the image files to extract their key features. Every image file first passes through one or more noise reduction filters (e.g., a image blurring routine) to eliminate minor visual distractions and is then analyzed with edge detection techniques to determine the features of the image. Major vertices of the image (i.e., visual keys including intersections of edges of the image) are analyzed to determine the pattern of the vertices or the "fingerprint" of the image. The fingerprint may be rotated and translated to develop a normalized vertex map. A matching algorithm weights the possible matches between the visual key signature of the image being analyzed and those within a database of known signatures looking for a statistically likely match. If none is found, the image file can be reprocessed with different criteria for noise filtering and edge detection until either a match is found or the image is deemed to be unknown. Those skilled in the art will recognize that the analysis performed to find a visual key signature for the image is similar to analyses performed by conventional fingerprint matching programs such as used by law enforcement organizations.

Additional information can be gleaned from an image by using a template system to highlight areas of an image that may contain additional indexing information. These areas include static elements and dynamic elements. Areas of the image files that are common from image to image are considered to be static elements. Areas of the image files containing data types that change from image to image are considered dynamic elements. Data obtained from the static elements can be used to verify that the correct index analysis template is being used and to further enhance indexing. The data in the static elements may include information such as page number, titles, descriptors and form identifiers. Dynamic elements may be analyzed using optical character recognition analysis to identify keywords, phrases and sentences in addition to their frequency enabling further indexing and identification of an image as part of a specific subset within a record. Once the document is indexed, a new watermark including the index identifier may be applied to the document. Alternatively, it envisioned an existing watermark can be modified to include the index identifier.

The following examples will illustrate the invention.

EXAMPLE 1

Structuring a Health Diagnostic Program

An example of the health diagnostic program of the present invention may be structured in a variety of ways. One example, though not intended to be limiting, includes four elements. These elements include: 1) a diagnostic questioner, 2) question codification, 3) stratification of body parts, and 4) weight analysis of responses to diagnostic questions.

1) Questioner

Not all questions must be applied to each query. Some questions may require repetition at different points in the process to ascertain the validity and consistency of responses, and confirm interviewee understanding of the question. This approach makes the process programmable, statistically analyzable and standardizable. Six areas are considered, divided into sectors, subsectors, sections and subsections as follows:

1-What
2-Where
3-When
4-Whom
5-How
6-Why

2) Question Codification

Questions are codified to facilitate organization of the information and programming by using a number code. In this particular embodiment, at least ten digits are used, although more digits may be necessary based upon the number of questions. A full historical interview may be obtained by combining the coded questions. With sufficient reiterations, a relatively high degree of certainty can be reached towards the correct diagnosis being included in the list of potential diagnoses.

Table I illustrates exemplary code ranges used to identify answers to diagnostic questions and are suffixed (alternatively, the codes may be prefixed) to a diagnostic question code and used in the differential evaluation of potential diagnoses. While an individual is only permitted to answer "yes" or "no" to a question, the diagnostic program can construct complex codes that are invisible to the individual that are based upon a plurality of symptoms. The codes in addition to "yes" and "no" also include "neither," "both or all," "and,"

"none," and "or." The complex codes are assigned to complex questions for constructing a differential ranking of diagnoses.

TABLE I

Answer Codes

| Answer | Code |
|---|---|
| no | 000 |
| yes | 111 |
| neither | 001 |
| both or all | 011 |
| and | 100 |
| none | 010 |
| or | 110 |

The diagnostic questions are grouped by symptoms and signs organized into organs or systems. Given a single or a multiplicity of symptoms, each symptom is addressed independently at first. Lists of grouped characteristics of each symptom are presented for selection (yes or no for each alternative). Subsequent questions refine the elicited characteristics with yes or no answers. The full symptom description is presented, including all the positives and pertinent negatives for approval (yes or no). This process is repeated for each symptom. Finally, the symptom descriptions are summarized and presented for approval (yes or no). A differential list of diagnoses is then presented in hierarchical order from most likely to least likely.

Digital areas are codified in Table II illustrating exemplary code ranges for the overall diagnostic program and the segregation and recognition of meaning.

TABLE II

Overall Diagnostic Program Codes

| AREA | DIGITAL CODE |
|---|---|
| Symptoms | 00000000001 to 19999999999 |
| Signs | 20000000000 to 29999999999 |
| Laboratory data | 30000000000 to 39999999999 |
| Imaging data | 40000000000 to 49999999999 |
| Family history, Symptom history, genealogy, vaccines | 50000000000 to 59999999999 |
| Medications and drugs | 60000000000 to 64999999999 |
| Surgical therapies | 65000000000 to 69999999999 |
| Diagnosis | 90000000000 to 99999999999 |
| etc. | |

Diagnostic program areas are subdivided into sectors, sub-sectors, sections, and sub-sections. Table III illustrates exemplary code ranges that are used to define sectors.

TABLE III

Sector Codes

| AREA | DIGITAL CODE |
|---|---|
| pain | 00000000001 to 000000005000 |
| cough and expectoration | 00000005001 to 000000010000 |
| chills and sweats | 00000010001 to 000000015000 |
| temperature | 00000015001 to 000000020000 |
| malaise | 00000020001 to 000000025000 |
| weight | 00000025001 to 000000030000 |
| eye and visual disorders | 00000030001 to 000000035000 |
| ear and auditory disorders | 00000035001 to 000000040000 |
| sensory | 00000040001 to 000000050000 |
| motor/muscle | 00000050001 to 000000060000 |
| nose and olfactory disorders | 00000060001 to 000000065000 |
| coordination | 00000065001 to 000000075000 |
| balance | 00000075001 to 000000085000 |

TABLE III-continued

Sector Codes

| AREA | DIGITAL CODE |
|---|---|
| growth | 00000085001 to 000000095000 |
| skin | 00000095001 to 000000110000 |
| tongue and taste disorders | 00000110001 to 000000120000 |
| mouth | 00000120001 to 000000125000 |
| teeth | 00000125001 to 000000130000 |
| neck | 00000130001 to 000000140000 |
| chest | 00000140001 to 000000145000 |
| breast | 00000145001 to 000000150000 |
| heart | 00000150001 to 000000165000 |
| circulation | 00000165001 to 000000175000 |
| lungs | 00000175001 to 000000185000 |
| respiratory | 00000185001 to 000000200000 |
| upper G.I. | 00000200001 to 000000205000 |
| stomach | 00000205001 to 000000210000 |
| small intestines | 00000210001 to 000000215000 |
| large intestines and rectum | 00000215001 to 000000220000 |
| liver | 00000220001 to 000000225000 |
| pancreas | 00000225001 to 000000230000 |
| thyroid | 00000230001 to 000000235000 |
| parathyroids | 00000235001 to 000000240000 |
| adrenals | 00000240001 to 000000245000 |
| kidneys | 00000245001 to 000000255000 |
| ureters and bladder | 00000255001 to 000000260000 |
| testicles and male functions | 00000265001 to 000000270000 |
| uterus, ovaries and female functions | 00000270001 to 000000280000 |
| upper extremities | 00000280001 to 000000285000 |
| lower extremities | 00000285001 to 000000290000 |
| genetics | 00000290001 to 000000300000 |
| embryonic, fetal and gestation | 00000300001 to 000000310000 |
| neonatal | 00000310001 to 000000320000 |
| vaccines | 00000320001 to 000000330000 |
| addictions | 00000330001 to 000000340000 |
| bacterial infections | 00000340001 to 000000350000 |
| viral infections | 00000350001 to 000000360000 |
| fungal infections | 00000360001 to 000000370000 |
| vitamins | 00000370001 to 000000380000 |
| upper back | 00000380001 to 000000390000 |
| lower back | 00000390001 to 000000400000 |
| genetic disorders | 00000400001 to 000000410000 |
| cancer | 00000410001 to 000000420000 |
| leukemia and lymphomas | 00000420001 to 000000430000 |
| anemia and blood | 00000430001 to 000000440000 |
| diabetes and metabolic disorders | 00000440001 to 000000450000 |
| allergies | 00000450001 to 000000460000 |
| birth defects | 00000460001 to 000000470000 |
| sleep disorders | 00000470001 to 000000480000 |
| mental health disorders | 00000480001 to 000000490000 |
| cognitive disorders | 00000490001 to 000000500000 |
| convulsions/epilepsy | 00000500001 to 000000510000 |
| consciousness and syncope | 00000510001 to 000000520000 |
| head and headaches | 00000520001 to 000000530000 |
| etc. | |

Sector codes are further parsed into sub-sector codes. Table IV illustrates exemplary code ranges used to define sub-sectors.

TABLE IV

Sub-Sectors

| Area | Digital Code |
|---|---|
| acute pain | 00000000001 to 00000000010 |
| sub-acute pain | 00000000011 to 00000000020 |
| chronic pain | 00000000021 to 00000000030 |
| constant pain | 00000000031 to 00000000040 |
| sharp pain | 00000000041 to 00000000050 |
| throbbing pain | 00000000051 to 00000000060 |
| etc. | |

Similarly, sub-sector codes are further parsed into section codes. Table V illustrates exemplary code ranges used to define acute pain sector codes.

TABLE V

| Sections | |
| --- | --- |
| Area | Digital Code |
| sharply localized central acute pain | 00000000001 to 0000000003 |
| general area acute pain | 00000000004 to 00000000006 |
| radiating localized acute pain | 00000000007 to 00000000009 |
| etc. | |

Section codes are further parsed into sub-section codes. Table VI illustrates exemplary code ranges used to define sharply localized acute pain to general area acute pain subsections.

TABLE VI

| Subsections | |
| --- | --- |
| Area | Digital Code |
| sharply localized central acute pain | 00000000001 |
| sharply localized to the right acute pain | 00000000002 |
| sharply localized to the left acute pain | 00000000003 |
| general area central acute pain | 00000000004 |
| general area to the right acute pain | 00000000005 |
| general area to the left acute pain | 00000000006 |
| radiating localized central acute pain | 00000000007 |
| radiating localized to the right acute pain | 00000000008 |
| radiating localized to the left acute pain | 00000000009 |
| etc. | |

EXAMPLE 2

Diagnostic Questioning

1) Symptoms

Presenting symptoms: headache, fever, vomiting, feeling awful.

Sufficient information are generated according to the medical diagnostics program to reach, by logical progression of inclusion, potential diagnoses that can be ranked from most likely to least likely. Potential diagnoses are ranked by correlating information received from individuals regarding subsections of different sectors and diagrams or graphical information provided by the individual, in a pattern of basic questions such as what, where, when, whom, how, and why. Questions can also be analyzed in reverse to determine potential diagnoses, such that by eliminating what is not, what is left is what it may be a potential diagnosis in the order of least to most likely.

As an example, an individual may be initially asked general questions such as the individual's sex, age, height, weight and so forth.

Once general questions have been asked and answered, questions may be asked regarding health symptoms and the location of the symptoms being experienced by an individual. These questions would fall into the "what" line of questioning. An example of such a question would be, "Do you have a headache?" If an individual were to affirmatively indicate the presence of a headache, the location of the headache would be determined by "where" types of questions. For example, the individual would be asked if the headache pain is localized (restricted to one area or part of the head). If the individual answers affirmatively, follow-up Y/N questions are asked to determine what location of the head aches such as "Front?," "Back?," "Right side?," "Left side?," and "All?"

Further questioning determines they type of pain experienced (a "what" type of question). An example of which would be, "Is the pain acute (of very rapid onset or development)?"

In all questions and answers, an answer of "Yes" would append the code "111" to the end of the diagnostic question code. Thus, an answer to a question will contain three digits more than the diagnostic question code. Thus, a question regarding whether sharply localized acute pain was present would result in an answer code of 00000000001+111 for a "yes" answer or 00000000001+000 for a "no" answer.

Answering yes to the questions regarding whether the pain is localized and if the pain is acute immediately eliminates questions regarding 0000000004 to 0000000060. On the other hand, answering no to the questions brings up 0000000004, etc.

By utilizing graphics (i.e., body diagrams which are digitized for patterns) anatomical localization and symptom description can be matched, narrowing diagnostic alternatives.

2) Signs

A similar approach is used for signs, utilizing as many interactive methods as possible to elicit them and confirm the veracity of presence (positive) or absence (negative) by cross-referencing signs whenever possible. Important or indispensable signs can be triple weighted, lesser important are double weighted, and even lesser, simple weighted. With the advent of electronically acquirable signs (i.e., audio cardiovascular; pulmonary; electric, such as EKGs, EEGs; etc.) higher weights can be assigned to these findings.

The above process is repeated for family history, symptom history, genealogy, laboratory, imaging, and so forth.

3) Differential Diagnoses Process

Segregation of "yes" answers in one column and "no" answers in another initiates the process for differentiating the potential diagnoses (the "differential diagnoses process"). By suffixing (or prefixing) the codes for yes (111) or no (000) to a question's code, a complexed code is created that is compared with all the potential diagnoses. The diagnoses containing the complexed code as part of their description are then selected. This eliminates all the diagnoses that are not possible. By matching the "yes" answers with all potential diagnosis codes, the unmatched are eliminated. The matched diagnosis codes represent the positive findings. By matching the "no" answers to the potential codes the unmatched are eliminated. The unmatched codes thus represent the negative findings that further help define the differential diagnoses process.

Various combinations of positives (111) are given different relative weights. Similarly, combinations of negatives (000) are also given different weights. For example, absolutely essential complexed codes for a diagnosis are be given a triple weight; important complexed codes are given double weight; and non-essential or important complexed codes are given simple weights. The complexed code weights can be increased or decreased further by considering some of the characteristics present in a combination of symptoms.

The positive findings are used to select all the potential diagnoses. The negative findings are used eliminate potential diagnoses and to compliment the positive findings. The combination of positive and negative findings suggest all the potential diagnoses.

Relative weights assigned to different positive combinations set a hierarchy of potential diagnoses. The negatives are used to degrade the relative weights assigned to each potential diagnosis. Data acquired from the patient such as the patient's medical history, social history, family history, genealogy history, genetic constitution, laboratory and imaging tests, medications, medical and surgical therapies, demographics, location, past history, recently encountered incidence of illnesses, and any other factor that experience teaches may add or subtract to the probability of a diagnosis or its position in the realm of potential diagnosis are used to further modify or dampen the weighting. Thus, modifying and dampening information are used to refine hierarchy of the potential diagnoses.

After the potential diagnoses are weighted, a ranked list of diagnoses are presented that should include the correct diagnosis in a high percentage (e.g., at least 99%) of the occasions. The ranking can be further characterized by dividing the diagnoses into groups such as the diagnoses with the highest probability, the top 10% of the potential diagnoses having the highest weighting, the middle 60%, and bottom 30%. Color-coding the list of potential diagnoses can further highlight the groups.

Since the interactive interview is occurring simultaneously to the analysis, reiterative questioning can be generated to re-assess the weight of potential combinations to confirm or refute analytical assumptions. The reiterative questions become progressively more complex and complete, refining the diagnoses.

As personal computers and the Internet continue to improve in speed and technology, the interchange will appear to be a real time event. Absent an intimidating interviewer (i.e., health care provider) and surroundings, time pressure, or other constraining factors, it is anticipated that the interviewee will provide more accurate and reliable answers. The interaction can also be used as a practice interview prior to a real encounter, as a supplementary or a substitute interview which would be delivered to the health care provider, or as a check on the performance of the health care provider.

The medical diagnostic program also accounts for individuals who try to confuse the interview by providing false or incongruent data. Fabricated or incongruent data, if not accounted for, may lead to the impossibility of reaching a diagnosis. Manipulated data may lead to a wrong diagnosis. Anticipating the likelihood that such data will be entered by individuals, a caveat is posted at the beginning of the interaction warning of the possibility and disclaiming responsibility.

EXAMPLE 3

Insurance and Finance System

Financing of health care has been a controversial issue of care in the last century. The controversy persists into this century since a reasonable solution has not been developed. As it exists, the present system is on the verge of collapse. Current methods of financing health care are inefficient, expensive, inequitable, complex, and top-heavy. Patchwork repairs have been made throughout the last century, gradually worsening the process. A solution to the dilemma would be of substantial benefit to society.

To solve the problems associated with financing health care, a number of assumptions can be made to correct some of the potential inequities and barriers. Some of these assumptions include:
1) Health care insurance is a privilege obtained by participating financially in proportion to income and wealth.
2) Basic health care may be offered free at government or society's discretion to those too poor to participate financially. Provisions for such coverage may require covered individuals to fulfill defined behavioral commitment.
3) All participants are required to actively engage responsibly in their health care.
4) The financial burden is shared between employer and employees.
5) Financial rewards are shared between employer and employees.
6) Incentives, both positive and negative, are built into the system to effectuate paragraphs 4 and 5, as described above.
7) Level of coverage or benefits are defined by premiums.
8) The system is privately operated, independent of government, and insurance, financial, or health care industry. This structure permits the level of independence necessary for the system to remain fair, equitable, viable and available.

Individuals pay 40% of premium fee; employers pay 60% annually. The health care financing and insurance system of the present invention acts as a manager that collects fees, income data, verification of need for services, verification of services rendered, agreed fees, payments for services, conflict resolution, investment of moneys, and dividend payments.

All approved visits, interventions, etc. are covered at 60% of the agreed fees. The individual pays 40% of the fees with a maximum out-of-pocket expense of 10% of gross income per year. After the cap is reached, the health care financing and insurance system (manager) pays all approved expenses above the cap. Each account runs a continuous tally. At retirement or after a predetermined number of years, the contributions by the employee and the employer are tallied and total expenses subtracted. Positive accounts receive a formula-directed dividend from the invested residuals; negative accounts receive nothing.

In order for this structure to work, all payments for services would have to be directed through the health care financing and insurance system. The employee would be billed for the co-payment or a deduction made directly from the paycheck.

The system can also financially manage the premiums in a manner that may produce financial benefits to the patient, or the insured party if the patient is covered by the insured parties policy (e.g., the child of an insured parent). The pooled residuals are invested long-term on a 6 to 12 months trailing wait. Savings produced from premiums and payments exceeding health care expenses may be invested or used to purchase further health care or long-term coverage. At the predetermined time, capital and interests, are distributed between employee and employer. The distribution formula can be proportional to contributions or biased to favor employer or employee according to stipulated contractual agreements. The distribution may occur at predetermined time such as after 20 years, after retirement, or at an age of 59.5 years similar to a pension distribution.

Controls:
1) Income verification: The best way to verify income is to obtain data from a governmental agency, such as the Internal Revenue Service. Due to privacy issues, however, such data may be required to be done anonymously and/or by income tax brackets. Alternatively, the employer could submit data to indicate the gross income level. This approach would work well for singles with no other jobs; individuals with more than one job could underpay, though it would not pose a significant problem. For families with more than one source of income, voluntary declarations would be the easiest to obtain, however, such declarations could also be easily falsified.
2) Verification of need of services: Verification would be contributed by the system of the present invention.
3) Verification of services rendered: Verification would be contributed by the system of the present invention.
4) Agreed fees and payments could be controlled utilizing the insurance program of present invention.

5) Conflict resolution would require a panel of experts. The process would be enormously aided by the information contained in the system of the present invention. One strategy would be to present cogent arguments against an unapproved or not indicated therapy; if individuals insisted on obtaining such treatment, they would be responsible to pay 60-70% of costs and the health care financing and insurance system pays the difference.

6) Investment of monies and dividend payments require development.

Several of the elements described above may be used in another aspect of the present invention to form a medical records system 100 including a central computer 102 connected to a global computer network 104 having a medical records database 106. The database 106 contains individual medical records 112 of multiple patients. Each of the records 112 corresponds to only one of the patients. The system 100 further includes one or more patient computers 108 connected to the global network remote 104 from the central computer 102. Each of the patient computers 108 has a patient interface program adapted to permit a patient to input medical history and biographical information into the medical records database 106 and to authorize a health care professional to access at least a portion of the individual medical records 112 of the respective patient. The system 100 also includes one or more health care computers 110 connected to the global network 104 remote from the central computer 102. Each of the health care computers 110 has a health care professional interface program adapted to permit an authorized health care professional to access the portion of the individual medical records 112 for which the health care professional has authorization and to input additional patient medical history and biographical information into the corresponding individual medical record 112 of the database 106.

In one embodiment, the health care professional interface program is adapted to permit an authorized health care professional to input information into the corresponding individual medical record 112 of the database 106. The information may be social history, clinical findings, laboratory test results, imaging results, physiologic findings, biochemical findings, anatomic findings, psychological findings, psychiatric findings, pathological findings, genetic findings and phenotypic findings. Alternatively or in addition, the information may be diagnosis, conclusions, recommendations, treatments, procedures and outcomes.

Further, the health care computer may include a health care reference database containing information such as diagnostic and protocol data, toxicology data, allergy data, immunological data, developmental data, endocrine data, cardiovascular data, gastrointestinal data, respiratory data, renal data, reproductive data, musculoskeletal data, rheumatologic data, dermatologic data, otorhynolaryngologic data, ophthalmologic data, gynecologic data, urologic data, neurological data, psychological data, psychiatric data, hepatologic data, homological data, pediatric data, rehabilitative data, genetic data and phenotypic data.

The security features described earlier may be included in the databases. For example, the individual medical records may include a watermark providing information about the record. The watermark may include a 128 bit encrypted two dimensional bar code including information such as ownership information, information related to source, information related to origin, information related to subject matter, and information related to access rights of the associated record. In one embodiment, the central computer includes a central program adapted to analyze watermarks of individual medical records containing information such as record content, source, and specific data, and to index the record for redistribution and display. Further, the individual medical records may be stored in the database as an electronic document image in a lossless compression format.

The health care computer may also include a security program adapted to selectively limit an extent and type of information stored in the individual medical records based on a degree of confidentiality assigned by a health care provider to the medical record for limiting access to the information by the health care professionals. As in the previously described embodiments, the security program may identify and log each attempt to access records in the medical records database. Likewise, the security program may identify and log the patients and the health care professionals who enter and store new information in the medical records database.

As further described above, the medical records database may include a document image having an encrypted visual watermark providing information about the document image. The information provided about the document image may include information such as document ownership, origin, source, subject matter, and management of access rights. Further, the document image may include a bar code having at least 128 bits of encrypted data arranged in two dimensions.

In addition, the system may include a scanner for creating the document image from a source document. The document image can include an encrypted digital watermark embedded in a blank space of the image providing information about the image. For example, the information provided about the document image may consist of information about document ownership, origin, source, subject matter, and information about access rights.

As described above, the document image is stored in a lossless compression format.

In one embodiment, the central computer and/or the health care computer includes a program adapted to integrate the user and provider information to authorize recommended prescriptions, prescribe treatments, prescribe therapies, prescribe interventions, order laboratory tests, order imaging and/or perform studies.

The system described above may be used to perform a method for providing health care services to a plurality of patients. This method includes acquiring individual medical records from each patient, obtaining permission from a particular patient to store the individual medical record of that particular patient, storing records for which permission is obtained from the particular patient in a database on a central computer, obtaining authorization from a particular patient to grant a health care professional access to at least a portion of the corresponding individual medical record of that particular patient, and permitting the authorized health care professional to access the portion of the specific record in the database corresponding to the particular patient. In one embodiment, the method also includes permitting a health care professional authorized by the particular patient to modify the record of the particular patient. The record modification, the record storage, and/or the record access may be logged.

In one embodiment, the method includes permitting a payer approved by the particular patient to access the record of the particular patient to verify treatment. The method may also include analyzing the record of one or more of the patients to determine whether the record is extraordinary compared to the records of other patients. Further, the method includes authorizing recommended prescriptions, prescribing treatments, prescribing therapies, prescribing interventions, ordering laboratory tests, ordering imaging and/or performing studies. Payment for services may be authorized upon satisfaction of established parameters for services.

In one embodiment, permission to access information contained in the records is variable and depends on established parameters.

The present invention assumes the existence of a single payer and administrator (either public or private), and multiple users and providers of services and products. Interactions occur under rules designed to regulate access, modes of interactions, and duties of each party. The administrator/payer determines user eligibility, determines provider eligibility, determines reasonable costs for services and products, insures availability, strives to eliminate unnecessary use and abuse of services, monitors quality of services and outcomes, and Guides development of future services.

The user may be anyone who falls under the definition of allowed user. Thus, those falling within this group will change with circumstances and time. The administrator/payer defines the characteristics that enable users. The user receives the services provided under the condition that he will comply with all the established rules and regulations. The user may not be directly responsible for cost of services, although certain fees or fractional cost charges to the user are not necessarily excluded.

The administrator/payer may be any entity willing to perform the role, such as a company, a group, an association, a government or a department of government, or a quasi-governmental institution.

Access to services may be controlled by identifying cards, chips, or other physical means of identification, such as biometrics. The user is obligated to provide the necessary documentation to access services. Variable levels of service may be provided according to rules established by the administrator/payer.

Users are expected to seek services when necessary, use the provided services, products, therapies or treatments, and follow the issued instructions to obtain maximum benefit. It is anticipated users will report both beneficial and detrimental results or side effects. The user is proscribed from seeking or using services, products, or therapies or treatments under false guise or pretense, such as for abuse of therapies or to provide the products or services to another authorized or not authorized user or individual. The user is obligated to provide requested information truthfully, including archived medical and personal information, to permit the best possible evaluation of his condition and validity of request for services. The user is obligated to provide the requested information each and every time he seeks or requests approved services. The user is obligated to verify provider services and report discrepancies. The use is further obligated to allow review of his records, anonymously if possible, to further public needs.

To guide the acquisition, compilation and availability of information, the operators or managers may provide users with facilities and tools to carry out the needed functions. The facilities and tools may or may not be free of cost to users.

A desired goal of at least one embodiment of the present invention is to develop individual patient, self-generated, fully controlled and censored, centralized electronic medical and biographical records and medical diagnostic system. The system and information may be accessed by patients and health care professionals regardless of their affiliation with a particular hospital, clinic, or other health care provider.

In one embodiment, it is envisioned that the medical and biographical records and medical diagnostic system would be maintained, managed, stored and delivered by a totally independent institution, not affiliated with government, insurance or health care industry. By using common language and phrasing tailored to different levels of education and familiarity with medical and health terms, an individual could effectively utilize such a system to determine potential diagnoses prior to seeking medical attention, permit the individual to be better informed as to the potential medical specialty from which to seek assistance, and control the content of and access to the individual's medical record.

A self-generated record of present illness and pertinent information would also benefit individuals by allowing them ample opportunity to ponder and respond outside the presence of the health care provider, which can generates discomfort or uneasiness and may lead to confused, unconsciously withheld, consciously suppressed information (e.g., suppressed for fear of embarrassment) or miscommunicated medical and biographical information.

As medical records already exist for the majority of users, a portion of the invention also includes a method for acquiring and incorporating existing documents into the contents of the newly generated health care records. In a previous invention it is described a method for scanning paper documents belonging to an individual and appending a unique electronic watermark to the documents by finding a "white space", either real or virtual. This watermark label contains a 128 bit (minimum) encrypted two dimensional bar-code that refers to a database containing information regarding ownership, origin and source of the documents, subject matter, and access rights. In addition, distribution of documents and trail of such distribution may be controlled by additional watermarks added to the documents at the time of release. Access to documents is also audited and the trail is available for review by user on demand.

Additionally, utilizing sophisticated analysis software the watermark labeled documents can be indexed according to subject matter, origin, source, type of document, and specific data, further facilitating integration and use of these documents into the health care records.

A centralized electronic medical and biographical records and medical diagnostic system would also permit any health care professional to be aware of all of a patient's biographical and medical history that is relevant to treating the patient. Additionally, since the centralized medical and biographical records system would not be the property of any one health care provider, the individual medical records could be "owned" by individual patients. Thus, patients may authorize or deny access to their medical and biographical records or limit access to only portions of their medical record to specific health care professionals thereby controlling privacy of the patient and confidentiality of the patient's medical and biographical information as long as the provisions of the system allow the individual the power to restrict certain providers from access to information not pertinent to their functions. Patients would also benefit by being able to review and comment on the contents of their records input by others for substance and accuracy.

A centralized electronic medical and biographical records and medical diagnostic system would also be beneficial in reducing health care costs and being a foundation upon which health care programs may be based. By centralizing the medical history and records of a patient, reduced costs may be realized by avoiding repeating tests or prescribing medications or treatment that have been previously found to be unsuccessful or contraindicated. Thus, unnecessary treatments would be reduced, thereby reducing healthcare costs and making the system more affordable.

Though the information of each user is private and confidential, the user could agree to the availability and use of the stored information for evaluation of health care and public health care needs, analysis, planning, or for utilizing the services under defined sponsorships. It is anticipated that user privacy could be protected from public disclosure. However, should information generated by group or population analysis, or for public health care reasons, indicate a health care matter requiring intervention or preventive health care activities, the user could allow private and discrete approach from providers.

Heath care providers benefit from the availability of centralized, compiled and analyzed information provided by the users. In return, as participants in the system and to obtain remuneration for services, providers could obligate themselves to comply with all the requirements of the system, including submitting detailed, truthful and verifiable information of services, products, therapies and treatments provided. Such information could be submitted to the centralized electronic and biographical records of the users.

Health care providers benefit from the availability of programs that help them direct the investigation of patient complaints. Available databases, including pharmacologic actions, good and bad interactions and a history of previous reactions by the individuals to same or similar drugs; could be sued to reduce untoward interactions, intolerances and side-effects, and significantly reduce wastage. On the other hand, patients could be reassured that ongoing analysis of their particular response to drugs, or a combination of drugs, would be recorded and unnecessary, useless or wasteful trials would be reduced or prevented altogether.

Facilitating the flow of information, including providing software for the generation and integration of medical information by providers, would likely encourage full participation. Coupling reimbursement for services to generation of appropriate reports would further interest in participation.

The provided information can be analyzed for quality and quantity of information and for determination of services rendered and level of compensation. Should significant shortcomings or deviation from reasonable and/or acceptable patterns of treatment be noted, the provider could be counseled and/or excluded from the list of approved providers, the intent being to maintain quality of services and fiscal responsibility but not discrimination.

One of the elements of checks and balances in the system is user review of the entered data. Since the records belong to the user, if a user disclaims the veracity of the documented data upon reviewing the entries, denial of payment for services claim and subsequent investigation would be triggered. Any provider with multiple denial events could lose the privilege to participate in the program.

Another element of the system included the generation of standardized services, therapies, treatments for similar diagnosed conditions. To maintain actuality in a dynamically changing field, such as health care, groups of experts in each one of the fields of endeavors will routinely be reviewing and modifying the accepted patterns of evaluation, diagnosis and treatment and updating the algorithms that control approval of services and verification of quality, quantity of services and outcomes.

Even with the above checks, a user and a provider could agree to abuse the system. Single or multiple violations may escape detection; patterns of abuse may eventually become evident, however by comparing deviations of services from patterns of other health care providers. Substantial deviations can be automatically culled out, permitting close scrutiny of activity and much earlier detection of fraud than occurs in current systems. One potential remedy, for example, can be requiring a second opinion or review by an independent consultant selected by the operator or manager of the system, or the performance of laboratory studies to confirm a disorder or the intake of medications, and so forth.

Due to the explosive growth of medications, alternative brands, and generics, there is a real risk that even the best informed and intentioned of health care professionals may miss an unintended interaction or secondary effect of a medication added to other medications already in use or to an underlying condition. By integrating all available information for a given patient and referring to massively stored drug information, undesired events could be significantly reduced, albeit not eliminated completely, due to the inability to infallibly predict all the potential reactions of one particular individual to a given biochemical combination. In spite of being unable to completely avoid undesired events, the potential savings in terms of reduction of iatrogenic injury, wasted medications or therapies, and prevention of costly side effects are great.

Another potential application is allowing service reviews to be conducted remotely while still protecting privacy and confidentiality of the user and the medical and biographical data. The requesting reviewer can submit the necessary identifying data and permission from a user to obtain medical and biographical data. The identification server would select the secret random number assigned to that specific patient, select the required information and delete identifying data (i.e., names, nicknames, initials, birthdays, addresses, etc.) and submit anonymous records to the reviewer. Of course, a single user request would be difficult to disguise, but controls may be put in place to require multiple records be requested by any one reviewer, diminishing significantly the chance of individual identification. Because of this potential breach of confidential information safeguarding, the first alternative is more secure and the preferred one.

Combining user and provider generated health care records and allowing free information flow between the groups will encourage better communication between the two parties, reduce errors, unnecessary repetitions, delays and waste. Significant economies can be anticipated with such a structure while at the same time preserving confidentiality, portability and privacy of information.

Another aspect of the present invention is directed to a health care service system that comprises a single health care service administrator, multiple health care service users, multiple health care service providers, and a health care service user-controlled, medical and biographical records database maintained on a central computer connected to a global computer network. The medical and biographical records database would be accessible through the use of one or more computers connected to the global network and situated remotely from the central computer. A software program interface would provide authorized health care service providers access to the medical history and biographical information from the health care service user's medical and biographical records database and permits additional health care service provider-generated medical and biographical information to be input into the user's medical and biographical records database.

One aspect of the invention, therefore, is a single health care service administrator that will define, monitor and enforce the rules and of the health care service system. The health care service system will provide for the effective delivery and payment of health care services. The duties of the health care service administrator may include, but are not limited to:

1) Establishing rules for determining health care service user eligibility;
2) Establishing rules for determining health care service provider eligibility;

3) Establishing rules for the administration of the health care service system;
4) Determining reasonable costs for health care products and services;
5) Determining health care services that will be paid by the administrator or a third party;
6) Dispersing payment to health care service providers;
7) Ensuring availability of health care services;
8) Eliminating unnecessary use and abuse of health care services;
9) Guiding development of future services;
10) Monitoring health care service users' compliance with established rules of the health care service system;
11) Monitoring health care service providers' compliance with established rules of the health care system;
12) Assessing reasonable fees to health care service users, if necessary; and
13) Enforcing all rules of the health care service system.

Another aspect of the present invention is to require health care service users to input pertinent and accurate medical and biographical data into a health care service user-controlled electronic medical records database which is "owned" by the health care service user. In one preferred embodiment, the medical and biographical records database will be stored, maintained, and managed by an independent institution, not affiliated with government, insurance or the health care industry. The database will contain medical and biographical records of the health care service user that can be accessed by health care service providers specifically selected and authorized by the health care service user wherein the access will be controlled by a security program.

The duties of the health care service user in the health care service system may include, but are not limited to:
1) Inputting pertinent and accurate medical and biographical data into a health care service user-controlled electronic medical records database;
2) Seeking health care services only when necessary;
3) Authorizing certain health care service providers access to applicable information in their biographical and medical records database;
4) Using the provided services, products, therapies or treatments as prescribed by the health care service provider;
5) Reviewing data inputted by any health care service provider into the biographical and medical records database for accuracy; and
6) Reporting any inaccuracies in the data inputted by the health care service provider.

The health care service user will be precluded from seeking or using health care services, products, treatments or therapies under false pretenses such as for abuse of therapies or to provide the products or services to another authorized or unauthorized health care service user. The health care service user will be obligated to provide accurate personal, biographical and medical information to the health care service provider to permit the best possible evaluation of his condition and the validity of his request for health care service.

Another aspect of the present invention is to also require health care service providers to input pertinent and accurate medical and biographical data into the same health care service user-controlled electronic medical records database which is "owned" by the health care service user. The health care service provider must input all information relating to the treatment of the health care service user including detailed information of services, products, therapies and treatments provided. This allows a future health care service provider of the user to have access to current, accurate information relating to the health care service user's medical and biographical history that may be relevant to providing health care services to the user.

The duties of the health care service provider in the health care service system may include, but are not limited to:
1) Inputting pertinent and accurate medical and biographical data into a health care service user-controlled electronic medical records database;
2) Performing health care services in compliance with established rules of the health care system administrator; and
3) Inputting all health care services performed into a health care service user-controlled electronic medical record database.

A further aspect of the present invention includes a means for the health care service providers to generate an electronic medical record which is "owned" by the health care service provider.

Another aspect of the present invention is an automated medical diagnostic system for use by a health care service user. In a preferred embodiment, the medical diagnostic system would be stored, maintained, managed and delivered by a totally independent institution, not affiliated with government, insurance or the health care industry. Diagnostic questions and the potential responses can be stored on a central computer connected to a global computer network and differentially weighted according to their relative importance in determining a medical diagnosis. Remote computers communicate with the central computer via a software program interface wherein the interface program interactively displays to the health care service user a series of diagnostic questions stored on a central computer. The central computer retrieves the answers the user inputs in response to the diagnostic questions and correlates the user responses and the assigned relative weight of the responses to a list of potential diagnosis. The central computer then provides the list of potential medical diagnosis to the user via the global computer network and a remote computer. The diagnostic system uses common language and phrasing tailored to different levels of education and familiarity with medical and health terms. The health care service user can use the diagnostic system to generate a record of present illness thereby permitting the potential health care service user to seek the appropriate medical specialty thus eliminating unnecessary visits to certain unnecessary medical specialties.

Another aspect of the present invention is a method for entering and retrieving patient medical and biographical record information wherein medical, biographical, and security information are maintained for a plurality of individual health care service users in a medical and biographical records database on a centralized computer. The health care service user's medical and biographical information is entered into the medical and biographical records database through a computer remotely situated from the centralized computer. The service user's medical and biographical records security information is also entered in the medical and biographical records database through the remotely situated computer. A security program is executed which limits access to the medical and biographical records database to the health care service user entering medical and biographical information into their own records and to health care service providers specifically authorized by the health care service user to input additional medical and biographical information to the users' records. The execution of a security program also limits access to the medical and biographical records database to the health care service users retrieving medical and biographical information from their own records and to individuals specifically selected and authorized by the health care service user.

Yet another aspect of the present invention is an automated medical diagnostic system for use by a health care service provider. Though the information of each health care service user is private and confidential, the user must agree to the availability and use of his stored medical and biographical information for evaluation of future public health care needs. Evaluation of this information will be used to generate standardized services, therapies, and treatments for similarly diagnosed medical conditions. To maintain actuality, groups of qualified health care experts will review and modify the accepted patterns of evaluation, diagnosis and treatment. In a preferred embodiment, the medical diagnostic system will include quantitative indication of the relative success of past treatments with an associated diagnosis.

In view of the above, it will be seen that the several objects of the invention are achieved.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A medical records system comprising:
    a central computer connected to a global computer network having a medical records database thereon, said database containing individual medical records of a plurality of patients, each of said records corresponding to one patient of said plurality of patients;
    a patient computer connected to the global network remote from the central computer having a patient interface program adapted to permit a patient to input medical history and biographical information into the medical records database and to authorize a health care professional to access at least a portion of the individual medical records of the respective patient; and
    a health care computer connected to the global network remote from the central computer having a health care professional interface program adapted to permit a health care professional authorized by a patient from the patient computer to access the portion of the individual medical records for which the health care professional has authorization and to input additional patient medical history and biographical information into the corresponding individual medical record of the database.

2. A records system as set forth in claim 1 wherein the health care professional interface program is adapted to permit a health care professional authorized by a patient from the patient computer to input information into the corresponding individual medical record of the database, said information being selected from a group consisting of social history, clinical findings, laboratory test results, imaging results, physiologic findings, biochemical findings, an anatomic findings, psychological findings, psychiatric findings, pathological findings, genetic findings, and phenotypic findings.

3. A records system as set forth in claim 1 wherein the health care professional interface program is adapted to permit a health care professional authorized by a patient from the patient computer to input information into the corresponding individual medical record of the database, said information being selected from a group consisting of diagnosis, conclusions, recommendations, treatments, procedures, and outcomes.

4. A records system as set forth in claim 1 wherein the health care computer includes a health care reference database containing information selected from a group consisting of diagnostic and protocol data, toxicology data, allergy data, immunological data, developmental data, endocrine data, cardiovascular data, gastrointestinal data, respiratory data, renal data, reproductive data, musculoskeletal data, rheumatologic data, dermatologic data, otorhynolaryngologic data, ophthalmologic data, gynecologic data, urologic data, neurological data, psychological data, psychiatric data, hepatologic data, homological data, pediatric data, rehabilitative data, genetic data, and phenotypic data.

5. A records system as set forth in claim 1 wherein at least one of said individual medical records includes a watermark providing information about the record.

6. A records system as set forth in claim 5 wherein said watermark comprises a 128 bit encrypted two dimensional bar code including information selected from a group consisting of ownership information, information related to source, information related to origin, information related to subject matter, and information related to access rights of the associated record.

7. A records system as set forth in claim 5 wherein said central computer includes a central program adapted to analyze watermarks of individual medical records containing information selected from a group consisting of record content, source, and specific data, and to index the record for re-distribution and display.

8. A records system as set forth in claim 1 wherein at least one of said individual medical records is stored in the database as an electronic document image in a lossless compression format.

9. A records system as set forth in claim 1 wherein the health care computer includes a security program adapted to selectively limit an extent and type of information stored in the individual medical records based on a degree of confidentiality assigned by a health care provider to the medical record for limiting access to the information by the health care professionals.

10. A records system as set forth in claim 9 wherein the security program identifies and logs each attempt to access records in the medical records database.

11. A records system as set forth in claim 9 wherein the security program identifies and logs the patients and the health care professionals who enter and store new information in the medical records database.

12. A records system as set forth in claim 1 wherein said medical records database includes a document image having an encrypted visual watermark thereon providing information about the document image.

13. A records system as set forth in claim 12 wherein the information provided about the document image includes information selected from a group consisting of document ownership, origin, source, subject matter, and management of access rights.

14. A records system as set forth in claim 12 wherein the document image includes a bar code having at least 128 bits of encrypted data arranged in two dimensions.

15. A records system as set forth in claim 12 further comprising a scanner for creating the document image from a source document.

16. A records system as set forth in claim 12 wherein the document image further comprises an encrypted digital watermark embedded in a blank space of the image and providing information about the image.

17. A records system as set forth in claim 12 wherein the information provided about the document image is selected from a group consisting of information about the document ownership, origin, source, subject matter, and information about access rights.

18. A records system as set forth in claim 12 wherein the document image is stored in a lossless compression format.

19. A records system as set forth in claim 1 where at least one of the central computer and the health care computer includes a program adapted to integrate the user and provider information to perform at least one of authorizing recommended prescriptions, prescribing treatments, prescribing therapies, prescribing interventions, ordering laboratory tests, ordering imaging and performing studies.

20. A method for providing health care services to a plurality of patients comprising:
    acquiring individual medical records from each patient of the plurality of patients;
    obtaining permission from a particular patient of said plurality of patients to store the individual medical record of that particular patient;
    storing said records for which permission is obtained from the particular patient in a database on a central computer;
    obtaining authorization from a particular patient of said plurality of patients to grant a health care professional access to at least a portion of the corresponding individual medical record of that particular patient; and
    permitting the health care professional who has been authorized by the particular patient to access the portion of the specific records in the database corresponding to the particular patient while preventing health care professionals other than those authorized by the particular patient to access records in the database corresponding to the particular patient.

21. A method as set forth in claim 20 further comprising permitting a health care professional authorized by the particular patient to modify the record of the particular patient.

22. A method as set forth in claim 21 wherein record modification is logged.

23. A method as set forth in claim 21 wherein copies of previous records are retained when a record is modified.

24. A method as set forth in claim 20 wherein record storage is logged.

25. A method as set forth in claim 20 wherein record access is logged.

26. A method as set forth in claim 20 further comprising permitting a payer approved by the particular patient to access the record of the particular patient to verify treatment.

27. A method as set forth in claim 20 further comprising analyzing the record of at least one of said plurality of patients to determine whether the record is extraordinary compared to the records of other patients within said plurality of patients.

28. A method as set forth in claim 20 further comprising imprinting a 128 bit encrypted two dimensional bar code in a blank space on the record of at least one of said plurality patients.

29. A method as set forth in claim 20 further comprising performing at least one of authorizing recommended prescriptions, prescribing treatments, prescribing therapies, prescribing interventions, ordering laboratory tests, ordering imaging and performing studies.

30. A method as set forth in claim 20 further comprising authorizing payment of services upon satisfaction of established parameters for services.

31. A method as set forth in claim 20 wherein permission to access information contained in the records is variable and depends on established parameters.

32. A method for providing health care services to a plurality of patients comprising:
    establishing rules for delivering and receiving health care services;
    acquiring individual medical records from each patient of the plurality of patients;
    requiring a particular patient of said plurality of patients to update the medical record by inputting current information;
    storing said records obtained from the particular patient in a database on a central computer;
    requiring authorization from the particular patient to grant a health care professional access to at least a portion of the corresponding individual medical record of that particular patient prior to receiving health care services from the health care professional;
    requiring the authorized health care professional to review the portion of the record in the database corresponding to the particular patient prior to the rendering of heath care services; and
    requiring the authorized health care professional to provide an accurate record of the health care services rendered.

33. A method as set forth in claim 32 further comprising authorizing payment of services only when the health care professional follows the established rules for delivering health care services.

34. A method as set forth in claim 32 further comprising authorizing payment of services only when the particular patient follows the established rules for delivering health care services.

35. A method for delivering health care while controlling interaction between users, providers, and payers through parameters and rules comprising:
    determining health care service user eligibility using a computing machine having access to a pre-determined criterion for health care service user eligibility saved on a machine readable memory;
    determining health care service provider eligibility using a computing machine having access to a pre-determined criterion for health care service provider eligibility saved on a machine readable memory;
    establishing rules for the administration of the health care service system;
    determining reasonable costs for health care products and services;
    determining health care services that will be paid by the administrator or a third party;
    dispersing payment to health care service providers;
    ensuring availability of health care services;
    eliminating unnecessary use and abuse of health care services;
    guiding development of future services;
    monitoring health care service users' compliance with established rules of the health care service system;
    monitoring health care service providers' compliance with established rules of the health care system; and
    enforcing all rules of the health care service system.

36. A method as set forth in claim 35 further comprising assessing reasonable fees to health care service users.

37. A health care process comprising:
    inputting pertinent and accurate medical and biographical data into a health care service user-controlled electronic medical records database stored on a machine readable memory;

seeking health care services only when necessary;

authorizing certain health care service providers access to applicable information in their biographical and medical records database;

using the provided services, products, therapies, or treatments as prescribed by the health care service provider;

reviewing data inputted by any health care service provider into the biographical and medical records database for accuracy; and reporting any inaccuracies in the data inputted by the health care service provider.

* * * * *